US012590043B2

(12) United States Patent
Huang et al.

(10) Patent No.: US 12,590,043 B2
(45) Date of Patent: Mar. 31, 2026

(54) COMPOSITIONS AND METHODS FOR IMPROVING PLANT GROWTH AND ABIOTIC STRESS TOLERANCE

(71) Applicant: RUTGERS, THE STATE UNIVERSITY OF NEW JERSEY, New Brunswick, NJ (US)

(72) Inventors: Bingru Huang, East Brunswick, NJ (US); Ning Zhang, East Brunswick, NJ (US); William Errickson, West Belmar, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 391 days.

(21) Appl. No.: 17/614,983

(22) PCT Filed: Aug. 14, 2020

(86) PCT No.: PCT/US2020/035409
§ 371 (c)(1),
(2) Date: Nov. 29, 2021

(87) PCT Pub. No.: WO2022/035410
PCT Pub. Date: Feb. 17, 2022

(65) Prior Publication Data
US 2023/0167036 A1 Jun. 1, 2023

(51) Int. Cl.
*C05F 11/08* (2006.01)
*C12N 1/205* (2026.01)
*C12R 1/01* (2006.01)

(52) U.S. Cl.
CPC .............. *C05F 11/08* (2013.01); *C12N 1/205* (2021.05); *C12R 2001/01* (2021.05)

(58) Field of Classification Search
CPC ................................. C05F 11/08; C12N 1/205
See application file for complete search history.

(56) References Cited

U.S. PATENT DOCUMENTS

| | | | |
|---|---|---|---|
| 4,245,432 A | 1/1981 | Dannelly | |
| 4,272,417 A | 6/1981 | Barke et al. | |
| 4,808,430 A | 2/1989 | Kouno | |
| 5,876,739 A | 3/1999 | Turnblad et al. | |
| 2003/0176428 A1 | 9/2003 | Schneidersmann et al. | |
| 2009/0308121 A1 | 12/2009 | Reddy et al. | |
| 2018/0153174 A1* | 6/2018 | Riley ..................... | A01N 63/30 |

FOREIGN PATENT DOCUMENTS

| | | |
|---|---|---|
| WO | 2002/028186 A2 | 4/2002 |
| WO | 2002/080675 A1 | 10/2002 |

OTHER PUBLICATIONS

Roland C. Wilhelm et al, "*Paraburkholderia madseniana* sp. nov., a phenolic acid-degrading bacterium isolated from acidic foresat soil", Int. J. Syst. Evol. Microbiol. 2020; 70:2137-2146.*

(Continued)

*Primary Examiner* — Wayne A Langel
(74) *Attorney, Agent, or Firm* — Howson & Howson, LLP; Kathleen D. Rigaut; Richard F. Kane

(57) ABSTRACT

Compositions and methods for enhancing plant growth and resistance to abiotic stressors are disclosed.

18 Claims, 26 Drawing Sheets
Specification includes a Sequence Listing.

(56) References Cited

OTHER PUBLICATIONS

Roland C. Wilhelm et al, "*Paraburkholderia solitsugae* sp. nov. and *Paraburkholderia elongata* sp. nov., phenolic acid-degrading bacteria isolated from forest soil and emended description of *Paraburkholderia madseniana*", Int.J. Syst. Evol. Microbiol. 2020; 70:5093-5105.*

International Search Report and Written Opinion, dated Oct. 13, 2020, issued in corresponding International Application No. PCT/US2020/035409.

Sawana, Amandeep et al., "Molecular signatures and phylogenomic analysis of the genus *Burkholderia*: proposal for division of this genus into the emended genus *Burkholderia* containing pathogenic organisms and a new genus *Paraburkholderia* gen. nov. harboring environmental species," Frontiers in Genetics, vol. 5, No. 429, Dec. 2014, pp. 1-22.

Young, Chiu-Chung et al., "Encapsulation of plant growth-promoting bacteria in alginate beads enriched with humic acid," vol. 95, No. 1, Sep. 2006, pp. 76-83.

Taylor, A.G. et al., "Concepts and Technologies of Selected Seed Treatments," Annual Review of Phytopathology, vol. 28, No. 1, 1990, pp. 321-339.

Power, B. et al., "Alginate beads as a storage, delivery and containment system for genetically modified PCB degrader and PCB biosensor derivatives of Pseudomonas fluorescens F113," Journal of Applied Microbiology, vol. 110, No. 5, May 2011, pp. 1351-1358.

Blum, A. et al., "Cell Membrane Stability as a Measure of Drought and Heat Tolerance in Wheat," Crop Science, vol. 21, No. 1, Jan. 1981, pp. 43-47.

Arnon, Daniel I., "Copper Enzymes in Isolated Chloroplasts. Polyphenoloxidase in Beta Vulgaris," Plant Physiology, vol. 24, No. 1, Jan. 1949, pp. 1-15.

* cited by examiner

COMPOSITIONS AND METHODS FOR IMPROVING PLANT GROWTH AND ABIOTIC STRESS TOLERANCE

CROSS-REFERENCE TO RELATED APPLICATIONS

This application claims priority to U.S. Provisional Application No. 62/854,539 filed May 30, 2019, the entire disclosures of the aforementioned application being incorporated herein by reference as though set forth in full.

INCORPORATION-BY-REFERENCE OF MATERIAL SUBMITTED IN ELECTRONIC FORM

Incorporated herein by reference in its entirety is the Sequence Listing submitted via EFS-Web as a text file named SequenceListing.txt, created May 14, 2020 and having a size of 2,518 bytes.

TECHNICAL FIELD

This application relates to compositions and methods for providing a benefit to a seed, a seedling of a plant, or a plant derived from the seed or seedling. For example, this application provides biofertilizer compositions comprising growth promoting bacteria, and synthetic combinations of seeds and/or seedlings with the bacteria and other components useful for promotion of plant growth. The bacteria containing compositions provide beneficial properties to the seed, seedling, or the agricultural plant derived from the seed or seedling, including beneficial properties related to metabolic, transcriptional, or proteome alterations, morphology, and the resilience to a variety of environmental stresses, and combination of such properties.

BACKGROUND

Fertilizers, based on both inorganic and organic substances, are employed worldwide in order to promote plant growth, development, and yield. Major factors limiting plant growth and productivity include abiotic stress, such as drought stress, salinity stress, nutrient deficiency, contamination with heavy metals, extreme temperatures and floods. For example, exposure to salt stress, drought conditions or nutrient deficiency generally causes a decrease in yields of plant material, seeds, fruit and other edible products. Crop losses and crop yield losses of major crops such as rice, maize (corn) and wheat, as well as losses of forest trees, caused by these stresses represent a significant economic and political factor and contribute to food shortages in many developing countries. Developing methods that render plants, for instance, salt stress-tolerant and/or resistant is a strategy that has the potential to solve or mediate at least some of these problems. Moreover, methods of enhancing soil nutrition and releasing plant nutrients from organic material could increase plant growth and alleviate environmental stress on plants.

Thus, there exists a continuing need to provide ways to render plants tolerant and/or resistant to abiotic stress and to enhance soil nutrients available to plants. It is an object of the present invention to provide a method to confer or increase abiotic stress tolerance and/or resistance to plants and to increase the availability of plant nutrients in the soil.

SUMMARY

A microbial inoculant biofertilizer composition comprising at least one microbial strain selected from *P. aspalathi*

WSF14 and *P. aspalathi* WSF23, and at least one non-naturally occurring agent, wherein the agent is least one of a cell protectant, an inert, a carrier, an emulsifier, a surfactant, and a polymeric matrix is disclosed herein. The biofertilizer composition can be employed in an effective amount to promote plant health, plant nutrition, and/or soil health in the presence of said agent.

In certain aspects, the one or more microbial species is lyophilized and optionally, can be encapsulated. The biofertilizer composition can further comprise one or more of mineral nutrients, amino acids, sugars, hormones, organic acids. In one embodiment, the composition is in a liquid formulation. In another embodiment, the composition comprises a carrier and/or a protectant.

Also provided is a method for increasing plant growth and/or productivity, the method comprising applying to a plant, plant part, plant seed, or to a soil in which the plant or plant seeds are grown, an effective amount of a microbial inoculant biofertilizer composition described herein.

In another embodiment, a method of enhancing a yield trait in a subject plant as compared to the yield trait of a reference or control plant, the method comprising contacting an effective amount of a microbial inoculant biofertilizer composition to the reference plant, plant part, plant seed, or surrounding soil with the biofertilizer composition of the invention at the effective amount is effective in enhancing the yield trait in the subject plant relative to the yield trait observed in the untreated reference or control plant. In certain approaches, the administering comprises contacting soil in the immediate vicinity of a plant, seedling, or seed with an effective amount of the biofertilizer composition.

In certain aspects of the method, the bacteria are present in a seed ball. The method can include administration of one or both of *P. aspalathi* WSF14 and *P. aspalathi* WSF23.

Also disclosed is a method of treating soil to improve plant growth, comprising applying the biofertilizer composition of the invention to said soil in an effective amount to improve growth of plants in said treated soil relative to plant growth observed in untreated soil.

In certain embodiments, *P. aspalathi* WSF14 and *P. aspalathi* WSF23 comprise SEQ ID NO: 1 and SEQ ID NO:2 respectively.

BRIEF DESCRIPTION OF THE DRAWINGS

FIG. 1A: Turf quality; FIG. 1B: Leaf relative water content; FIG. 1C: Membrane integrity/electrolyte leakage; FIG. 1D: Photochemical efficiency; FIG. 1E: Chlorophyll content; FIG. 1F: Root diameter.

FIG. 2A: Turf quality; FIG. 2B: Electrolyte Leakage; FIG. 2C: Photochemical efficiency.

FIG. 3A: Shoot biomass; FIG. 3B: Membrane integrity/electrolyte leakage; FIG. 3C: Root biomass; FIG. 3D: Root diameter; FIG. 3E: Root volume.

FIG. 4A: Shoot biomass; FIG. 4B: Root biomass; FIG. 4C: Root length; FIG. 4D: Root volume; FIG. 4E: Root surface area.

FIG. 5A: Root surface area; FIG. 5B: Root diameter; FIG. 5C; Root volume.

3

Figure 6A:
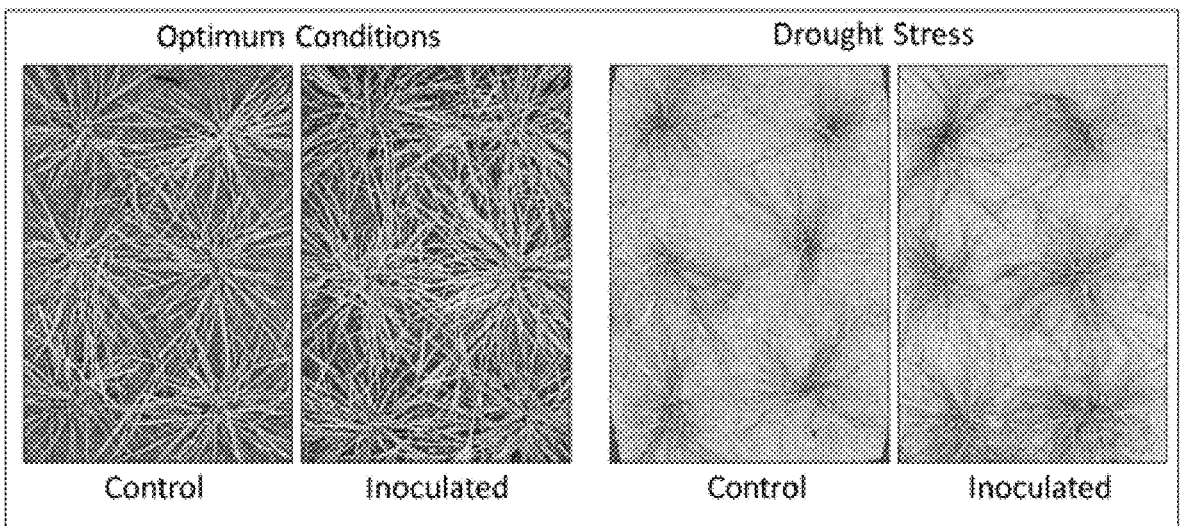
Figure 6B:
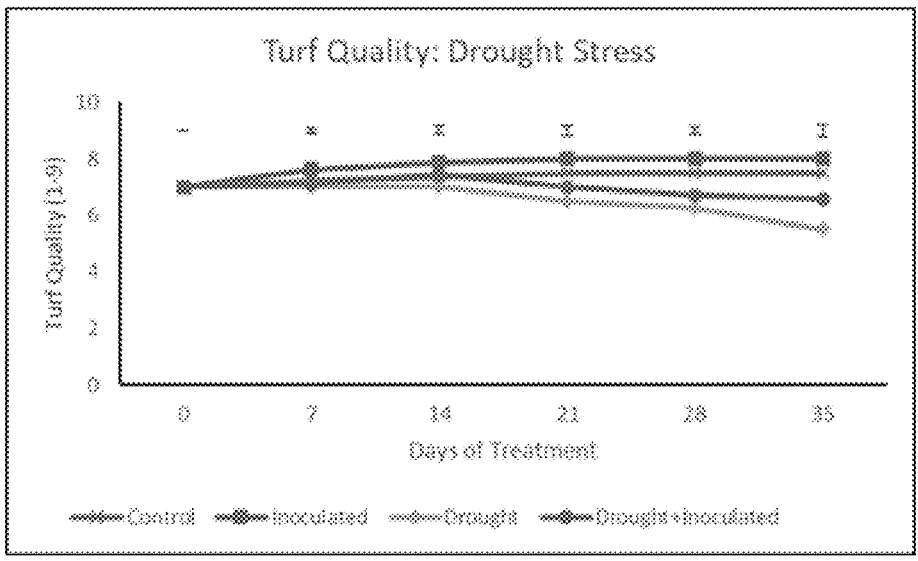
Figure 6C:
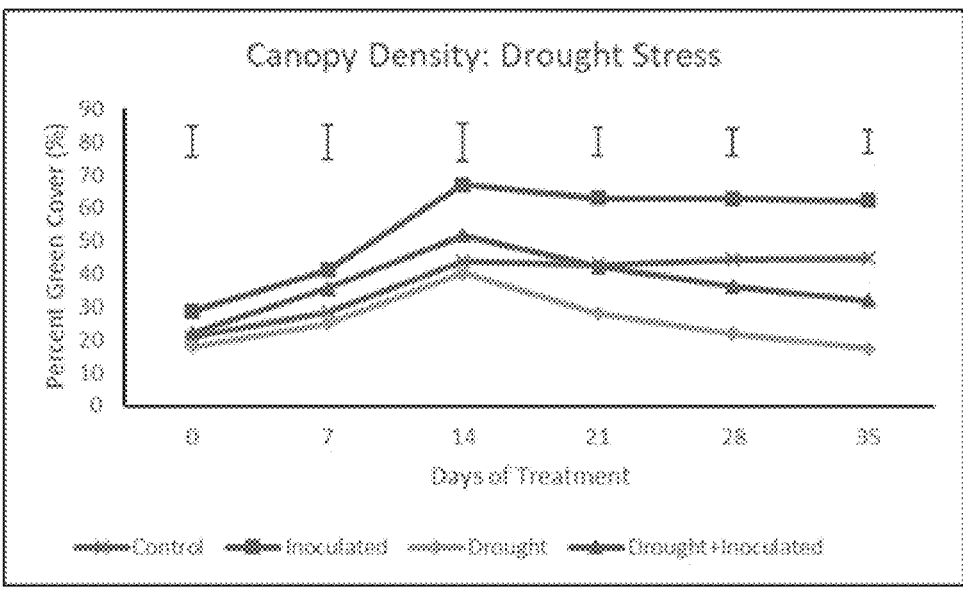
Figure 6D:
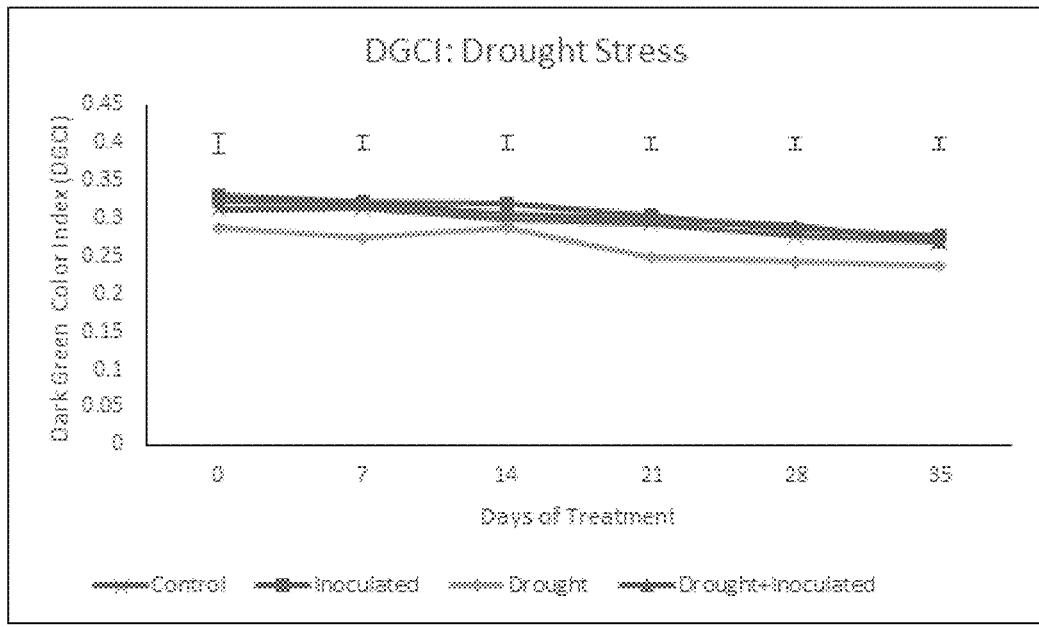
Figure 6E:
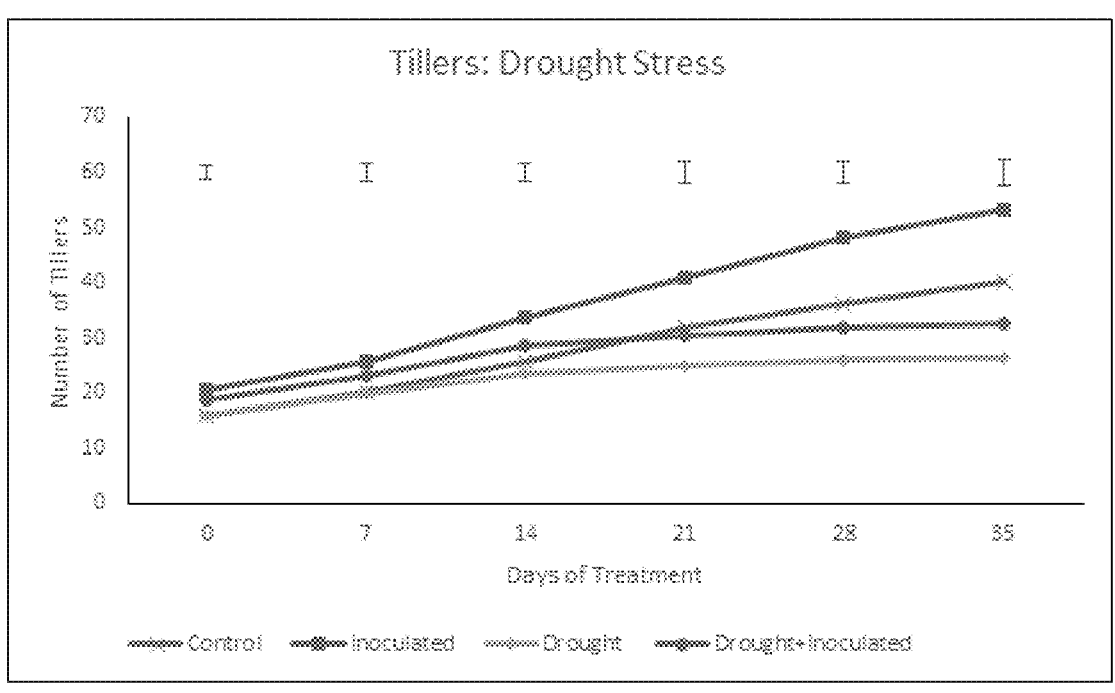
Figure 6F:
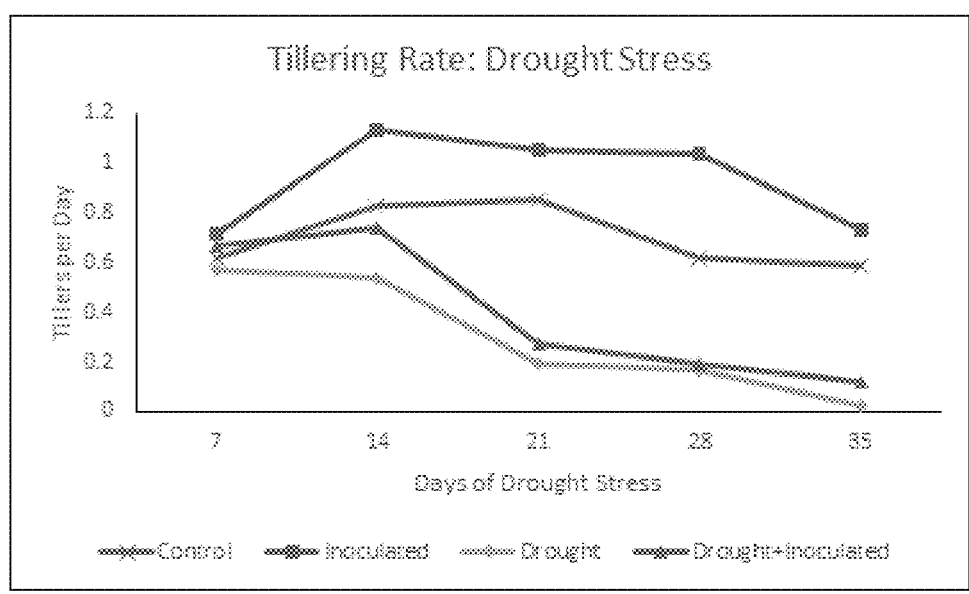
Figure 6G:
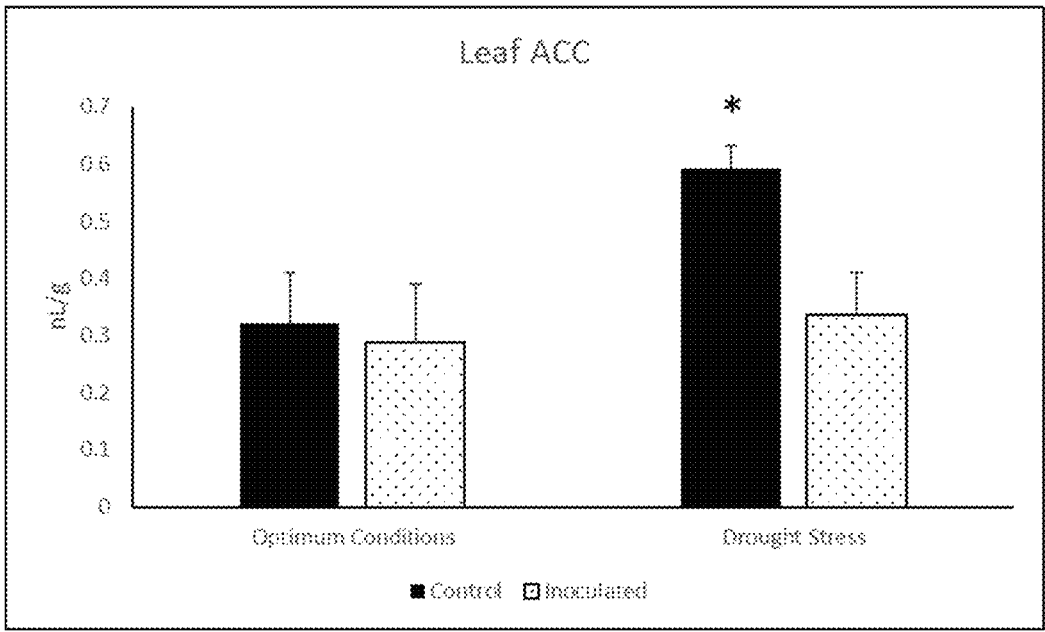
Figure 6H:
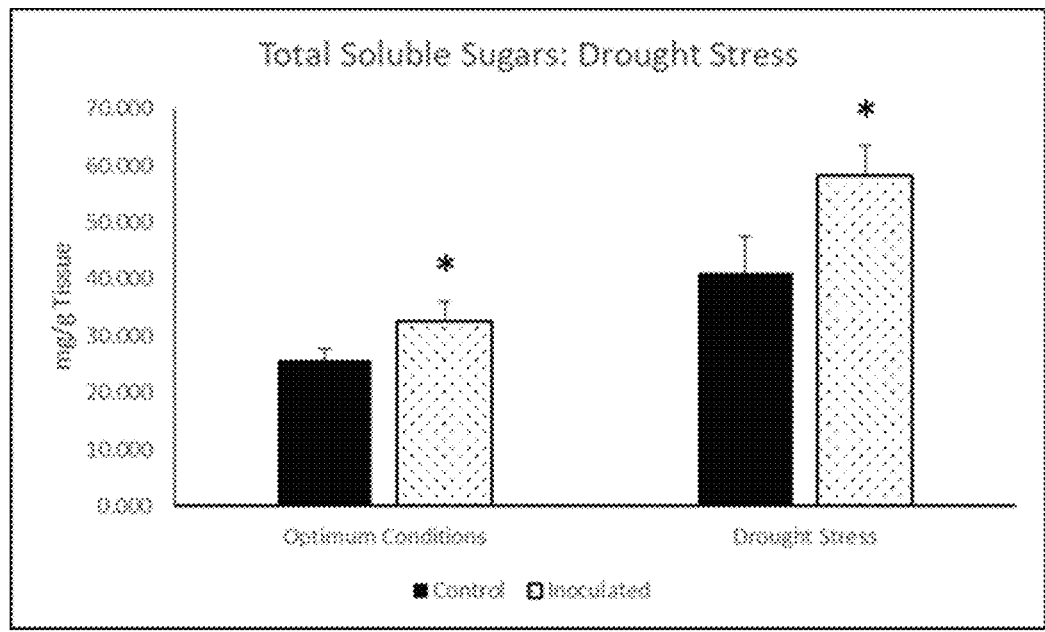
Figure 6I:
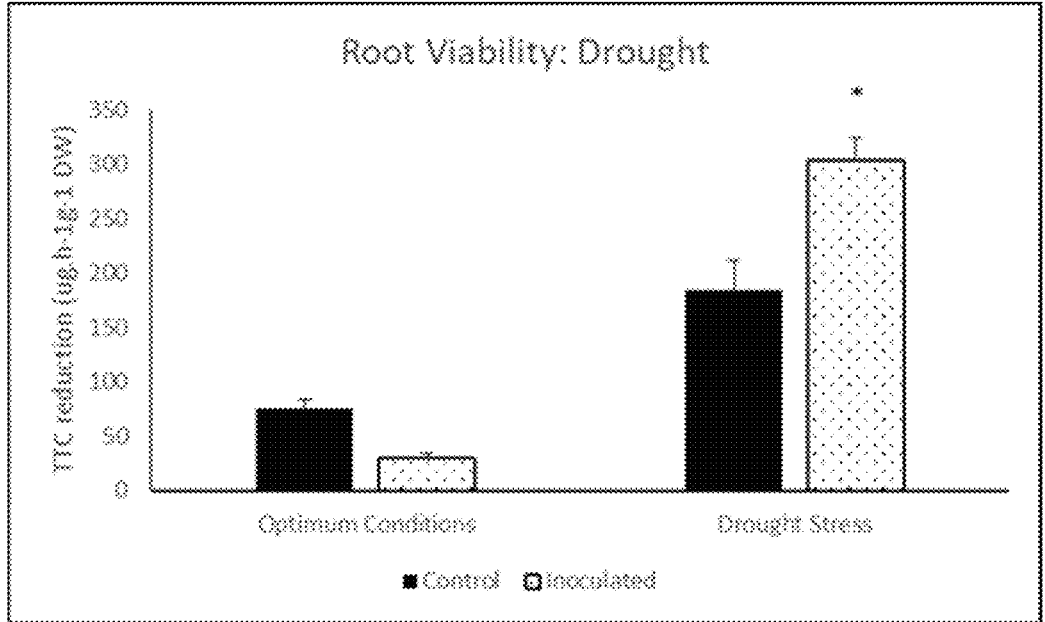

FIGS. 6A-6H: *P. aspalathi* WSF23 improves plant growth in drought and optimal conditions. FIG. 6A: Creeping bentgrass plants inoculated with WSF23 demonstrated enhanced tolerance to 35 days of drought stress conditions. FIG. 6B-6F: When compared to control plants during 35 days of optimal conditions or drought conditions, creeping bentgrass plants inoculated with WSF23 retained higher turf quality (FIG. 6B), higher canopy density (FIG. 6C), higher dark green color index (DGCI) (FIG. 6D), produced more tillers (FIG. 6E), and a higher rate tiller of production (FIG. 6F). FIG. 6G-6I: When compared to control plants after 35 days of optimal conditions or drought conditions, creeping bentgrass plants inoculated with WSF23 had lower levels of ACC in the leaves (FIG. 6G), higher levels of total soluble sugars in the crown tissue (FIG. 6H), and greater root viability (FIG. 6I) (* indicates significance at $p<0.05$).

Figure 7A:
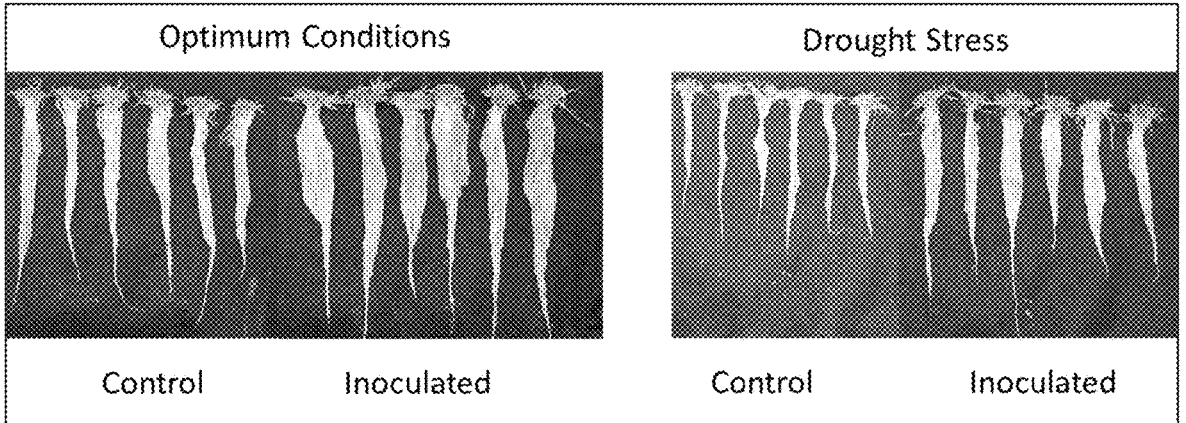
Figure 7B:
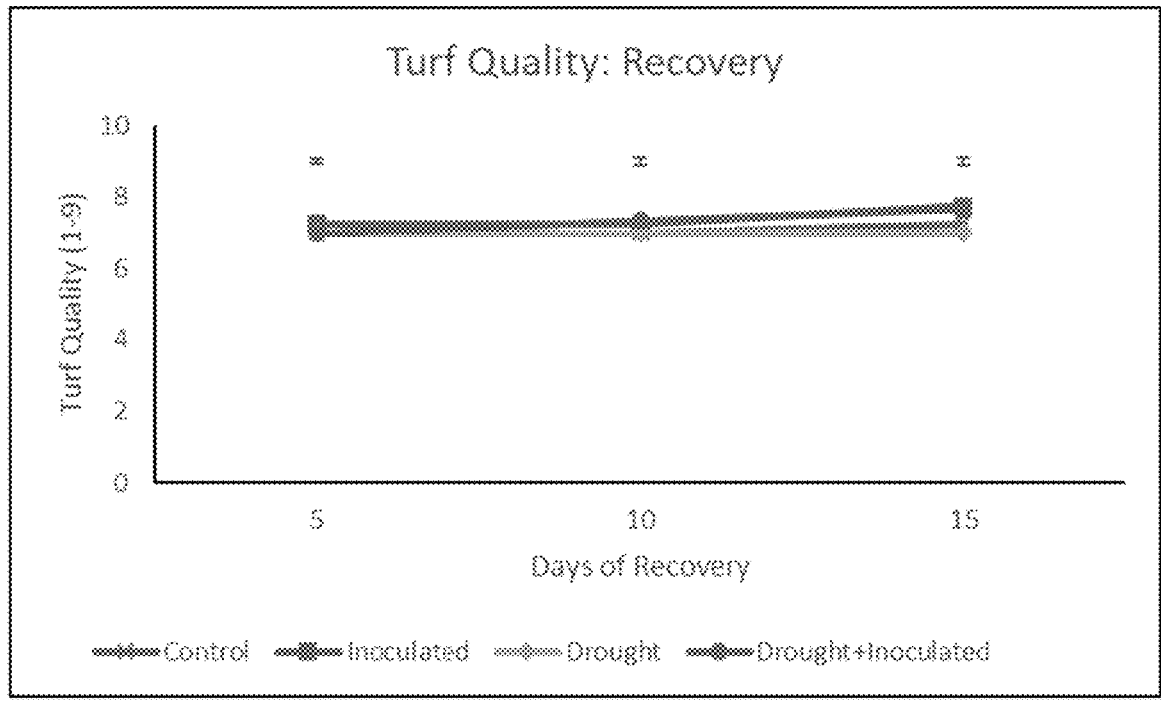
Figure 7C:
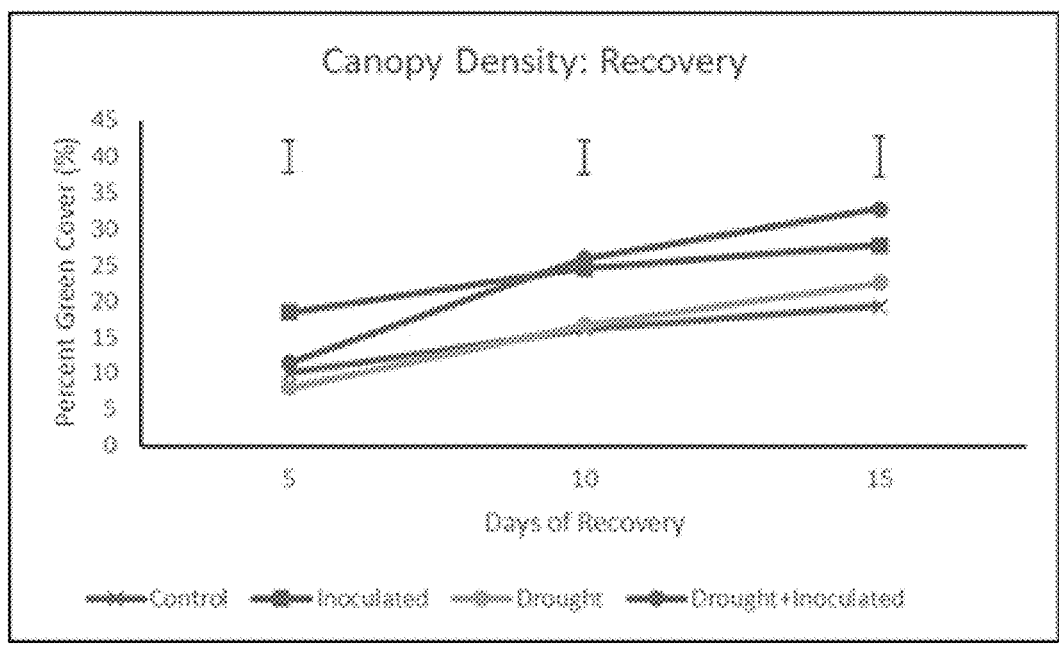
Figure 7D:
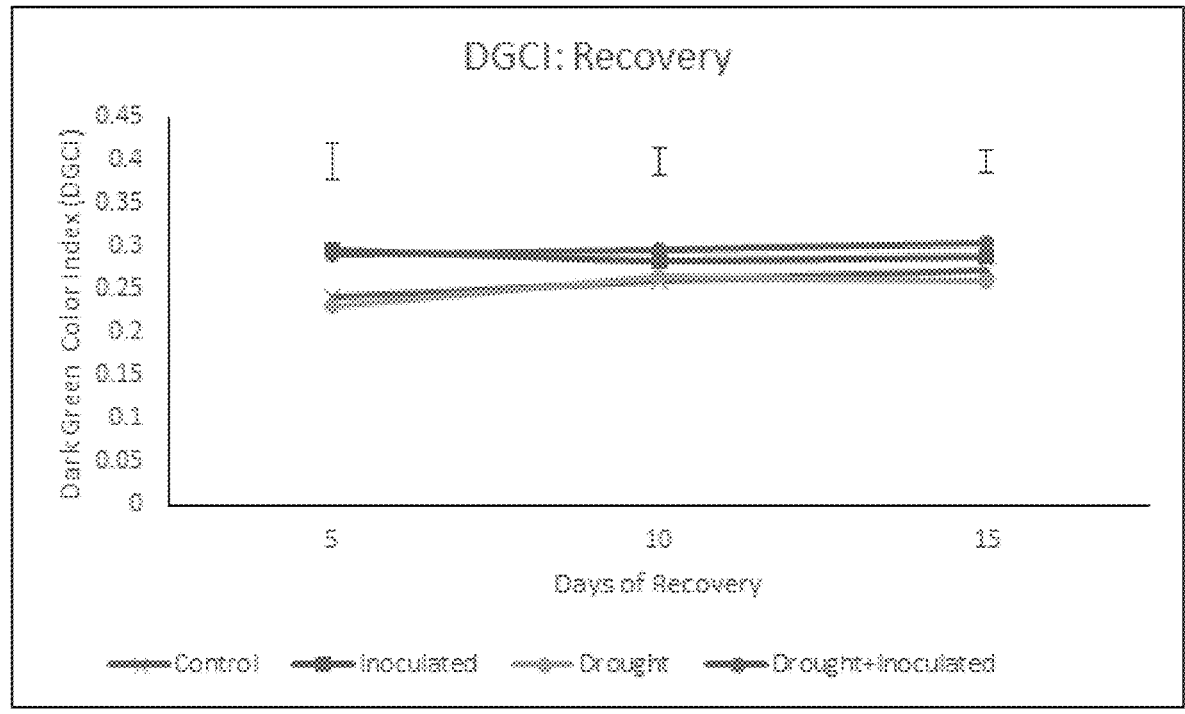
Figure 7E:
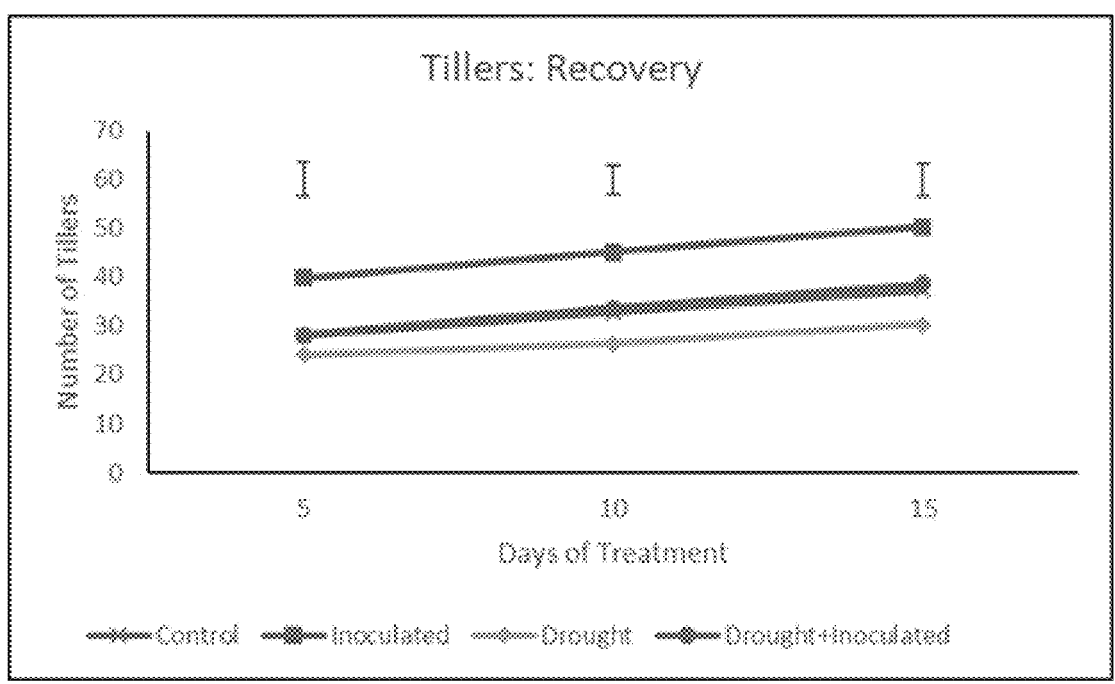
Figure 7F:
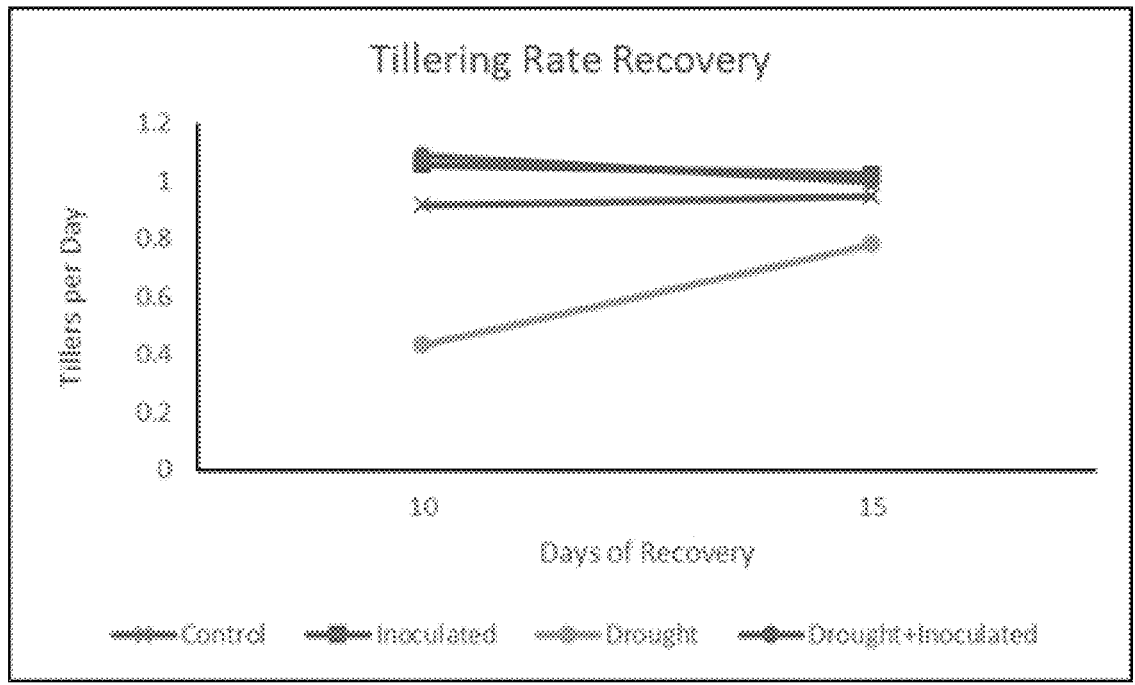
Figure 7G:
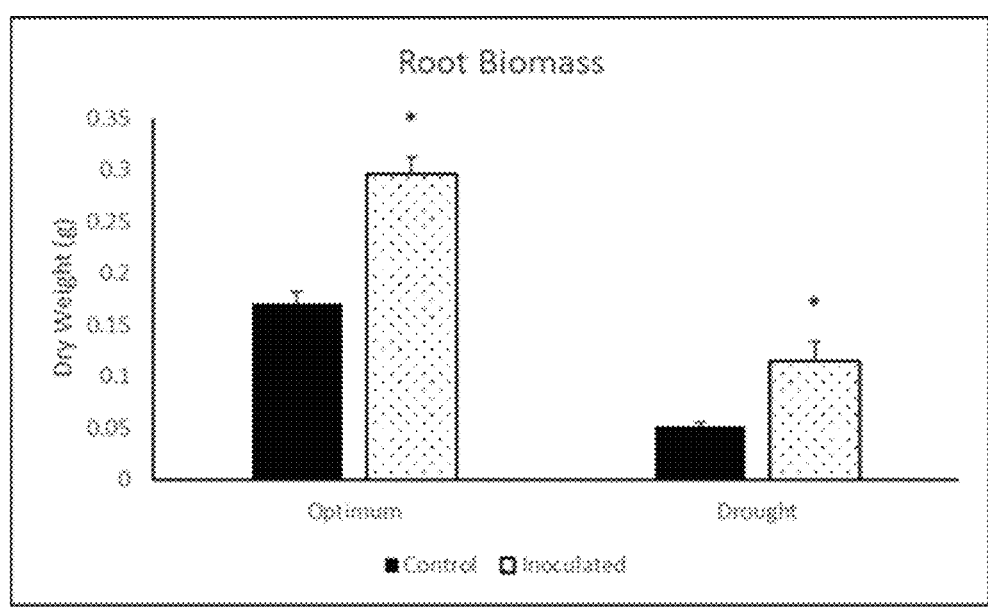
Figure 7H:
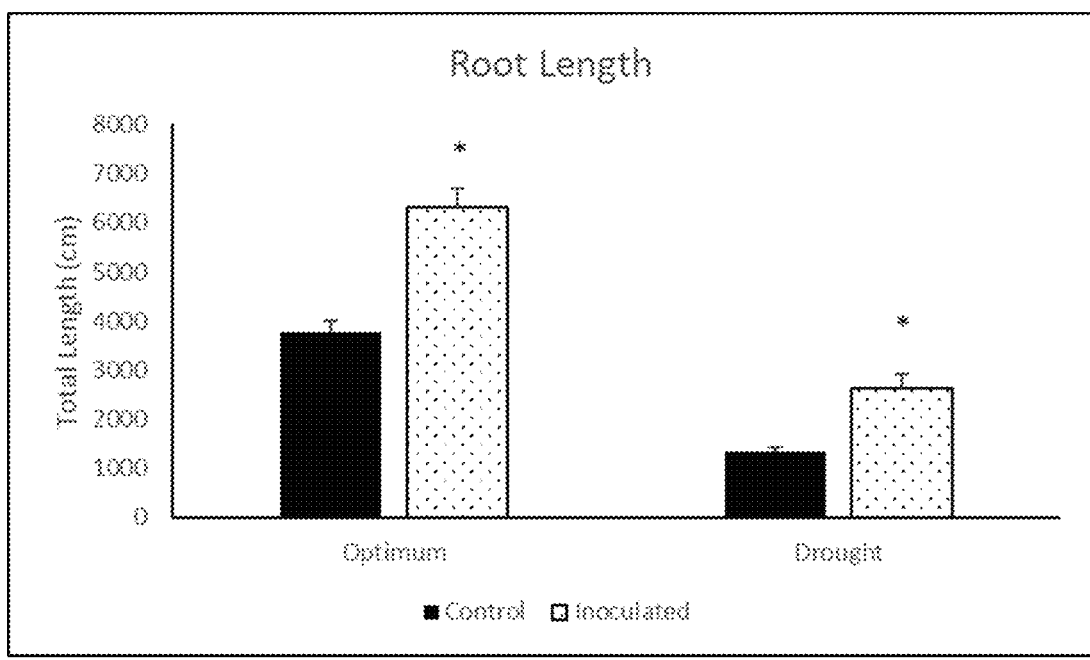
Figure 7I:
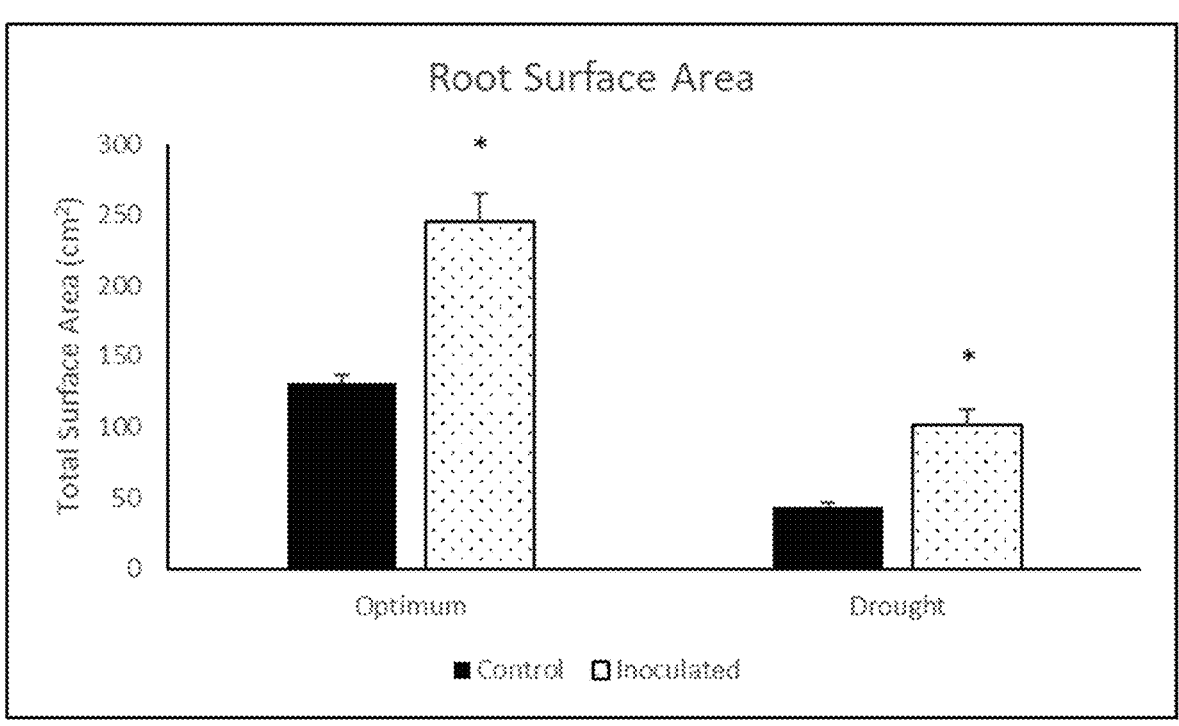
Figure 7J:
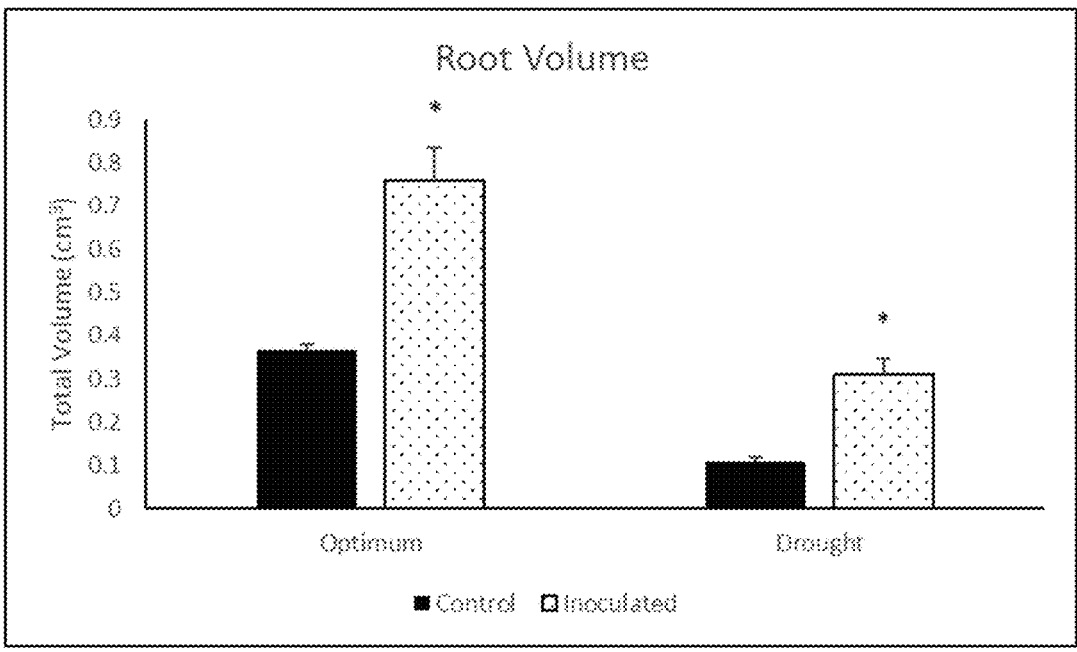
Figure 7K:
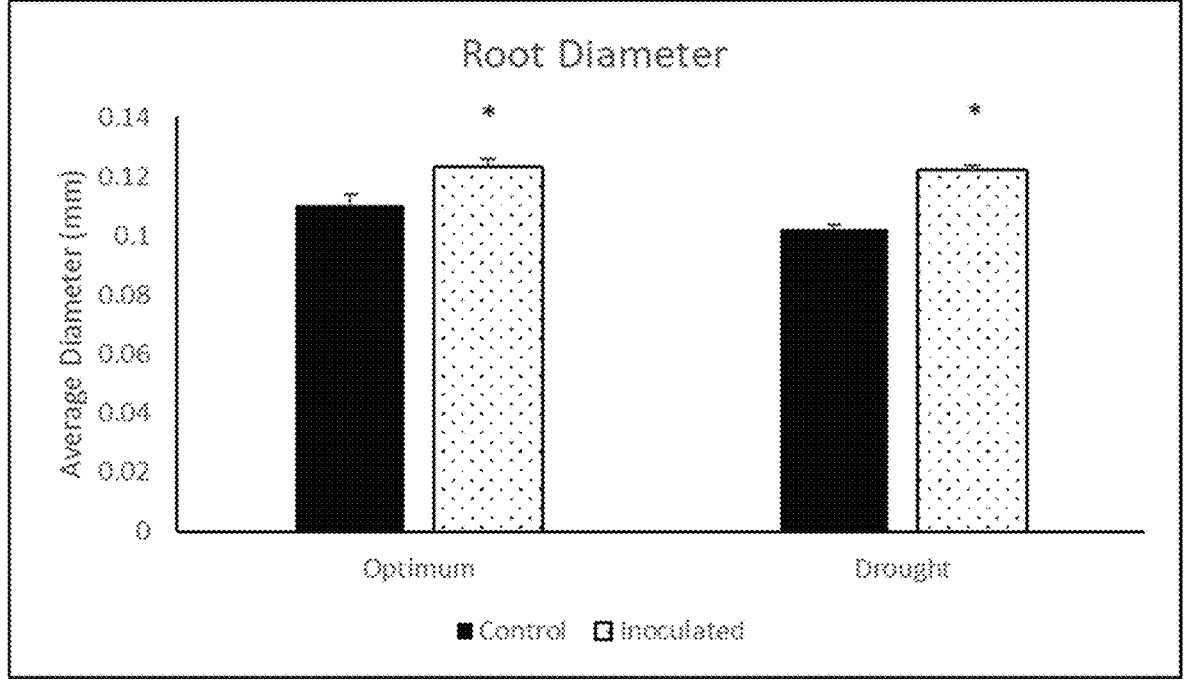

FIGS. 7A-7K. *P. aspalathi* WSF23 improves plant recovery post-drought. FIG. 7A: Creeping bentgrass plants inoculated with WSF23 demonstrated greater root growth than non-inoculated plants after 35 days of drought stress followed by 15 days of re-watering during the recovery period. FIG. 7B-7F: When compared to control plants upon re-watering, creeping bentgrass plants inoculated with WSF23 and subjected to drought stress had higher turf quality (FIG. 7B), greater canopy densities (FIG. 7C), higher dark green color index (DGCI) (FIG. 7D), more tiller production (FIG. 7E) and, tiller production at a higher rate (FIG. 7F). FIG. 7G-7S: When compared to control plants after 35 days of drought stress followed by 15 days of re-watering during the recovery period, creeping bentgrass plants inoculated with WSF23 had greater root biomass (FIG. 7G), length (FIG. 7H), surface area (FIG. 7I), volume (FIG. 7J), and diameter (FIG. 7K). (*indicates significance at $p<0.05$).

Figure 8A:
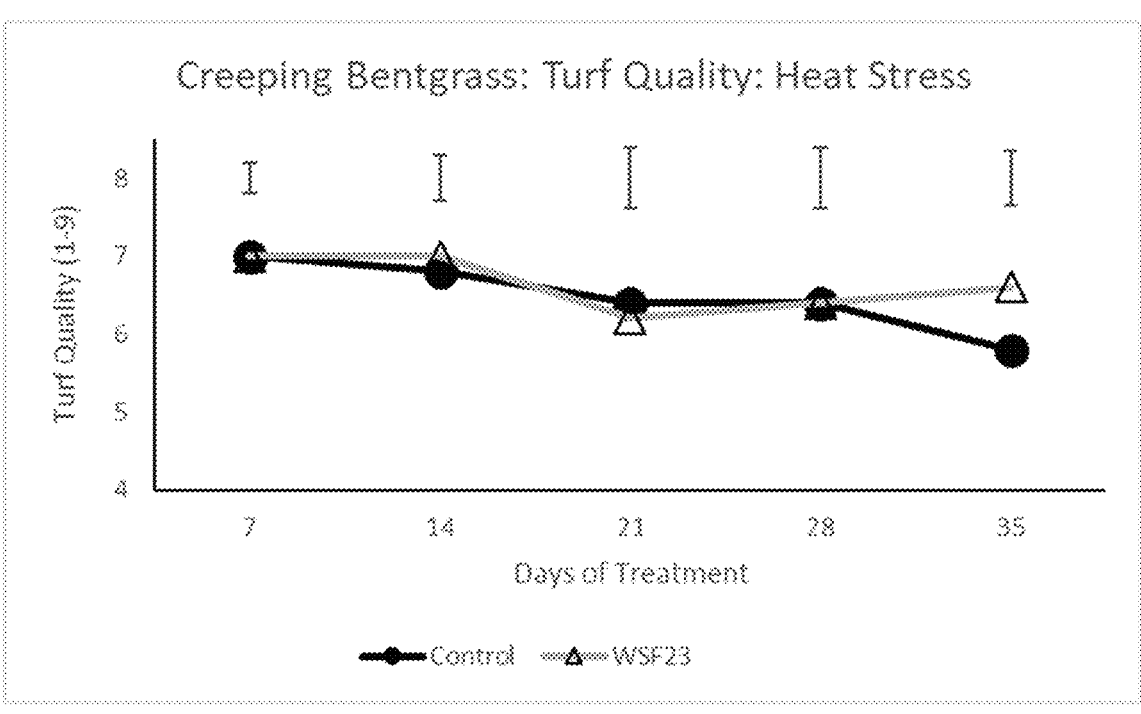
Figure 8B:
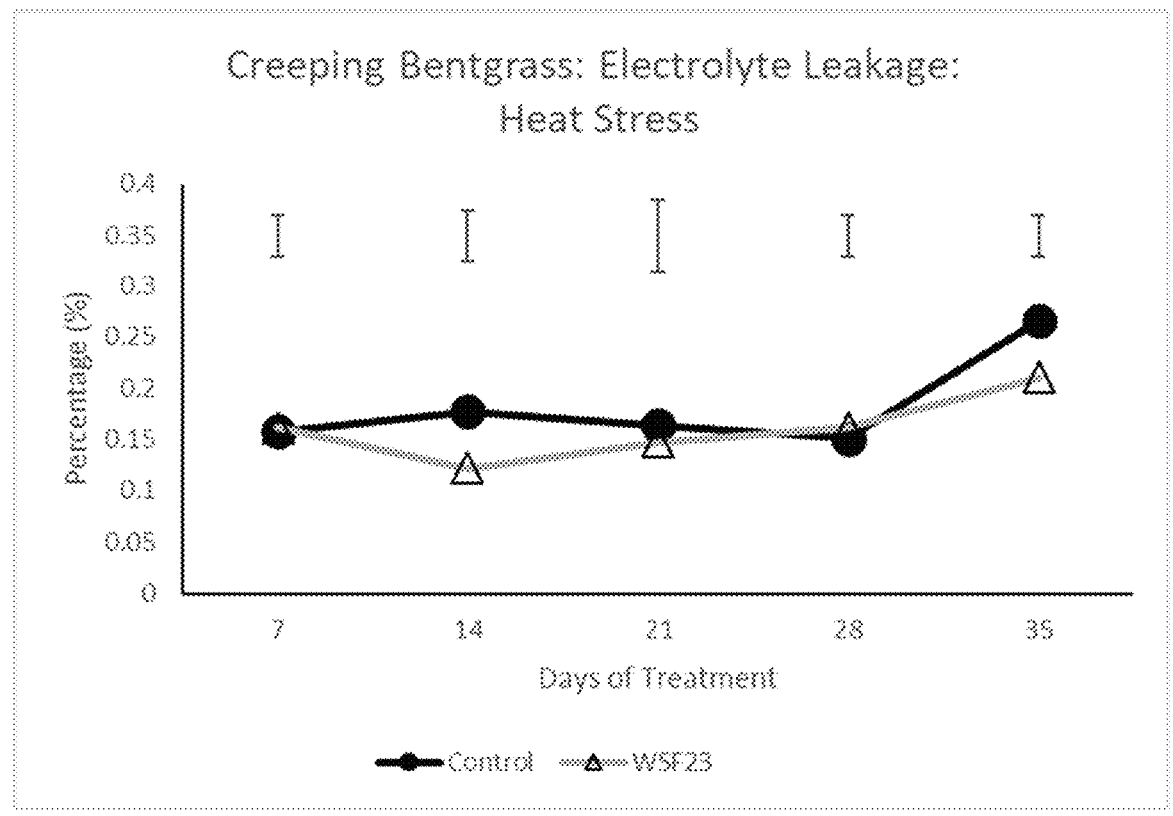
Figure 8C:
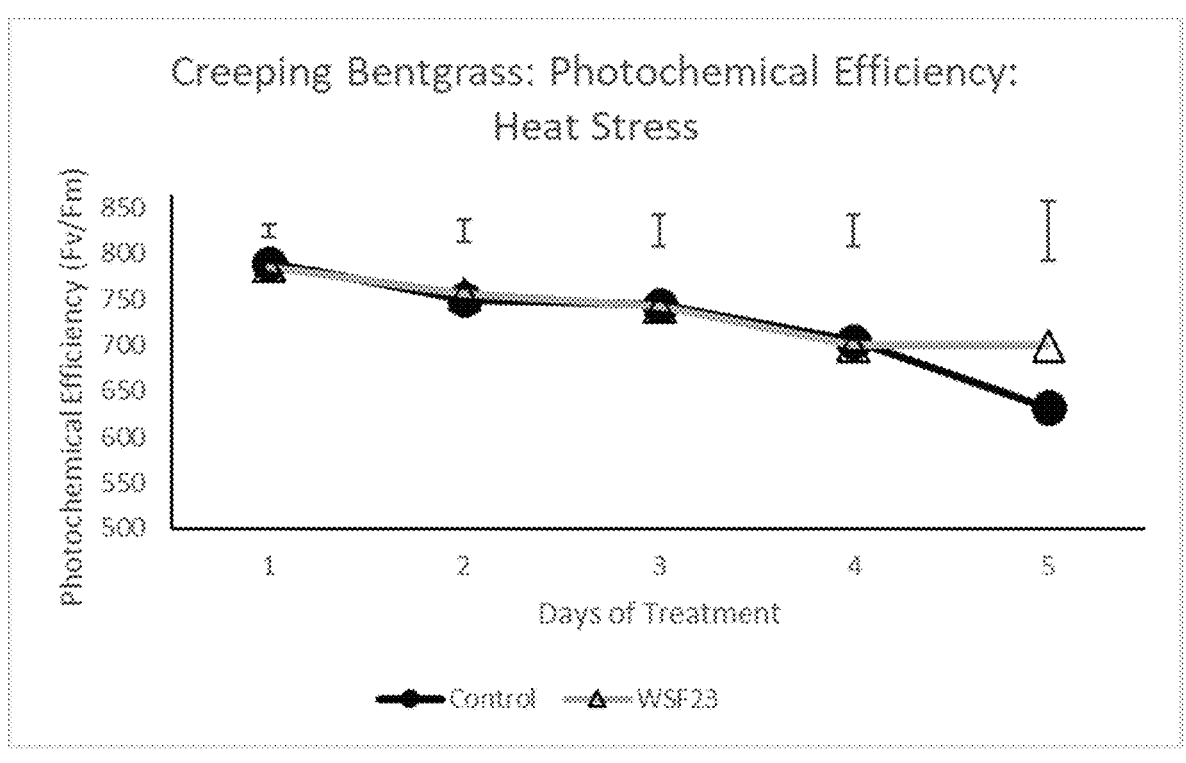
Figure 8D:
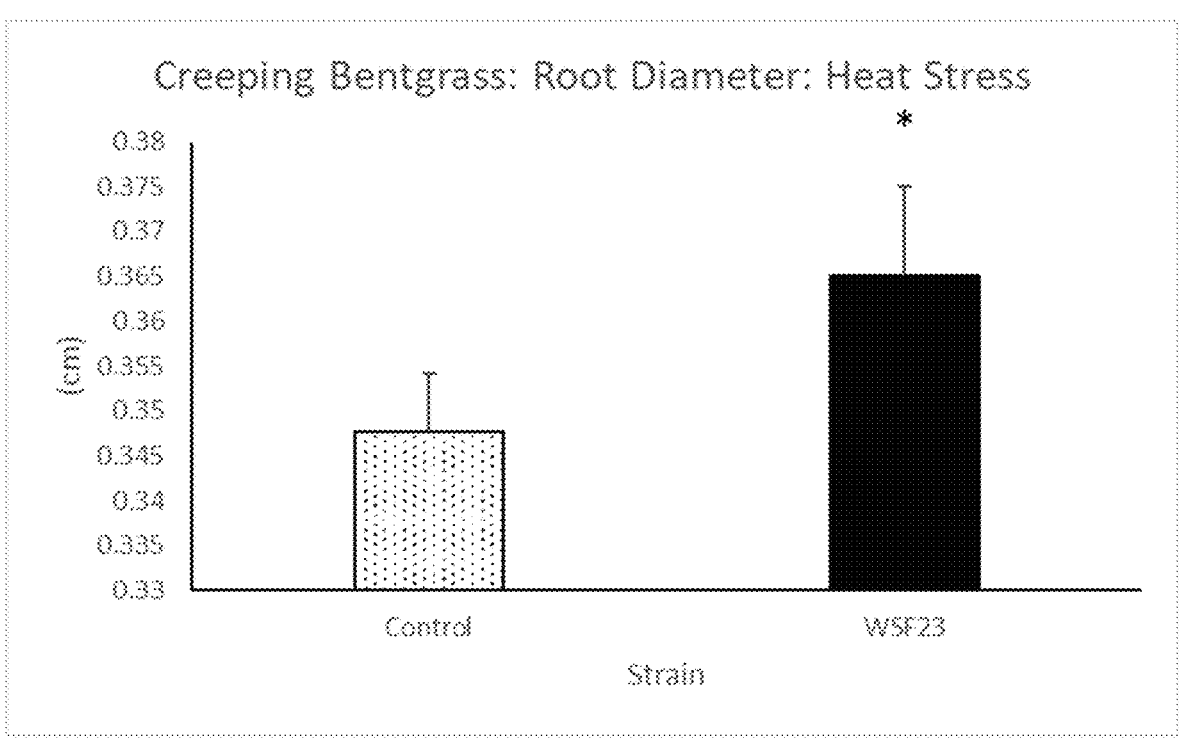

FIGS. 8A-8D. *P. aspalathi* WSF23 improves heat stress tolerance in creeping bentgrass plants. FIG. 8A: Turf quality; FIG. 8B: Electrolyte leakage; FIG. 8C: Photochemical efficiency; FIG. 8D: Root diameter.

DETAILED DESCRIPTION

Until 2014, *Paraburkholderia* and *Burkholderia* were classified in the same genus (Sawana et al. 2014, "Molecular signatures and phylogenomic analysis of the genus *Burkholderia*: Proposal for division of this genus into the amended genus *Burkholderia* containing pathogenic organisms and a new genus *Paraburkholderia* gen. nov. harboring environmental species.") These investigators were able to distinguish the *Paraburkholderia* genus from *Burkholderia* genus based on the presence and absence of specific molecular biomarkers. While *Paraburkholderia* species are not commonly associated with human infection, the *Burkholderia* genus contains pathogenic species.

*Paraburkholderia aspalathi* was discovered in 2014 by Mavengere et al (South Africa) by isolation from root nodules of *Aspalathus abietina* Thunb. Also, in 2014, *Burkholderia aspalathi* sp. nov., was isolated from root nodules of the South African legume *Aspalathus abietina* Thunb. This species was reclassified to *Paraburkholderia aspalathi* in 2017. See International Journal of Systematic and Evolutionary Microbiology, Validation List No. 173 (2017; 67: 1-3)

The present inventors have isolated two new strains of *P. aspalathi* which exhibit high levels of ACC-deaminase activity and auxin production that, when applied to certain plant parts, possess plant-growth promoting effects. Turfgrass, tomato, and corn plants inoculated with this species were found to have better growth rate and biomass production under non-stress conditions, and under abiotic stress, including without limitation, drought, heat, low fertility, and salinity conditions.

The invention also provides various compositions and methods for application of the biofertilizer to plant, plant parts, and soil.

The terms below are used throughout the application.

As used herein, the term "enhanced abiotic stress tolerance" refers to an improvement in the ability of a plant or plant part to grow, reproduce and/or survive under abiotic stress conditions, as compared to one or more controls (e.g., a native plant/plant part of the same species). "Enhanced abiotic stress tolerance" may refer to any improvement in a plant's or plant part's ability to thrive and/or endure when grown under abiotic stress conditions, including, but not limited to, decreased water loss, decreased accumulation of one or more reactive oxygen species, decreased accumulation of one or more salts, increased salt excretion, increased accumulation of one or more dehydrins, improved root architecture, improved osmotic pressure regulation, increased accumulation of one or more late embryogenesis abundant proteins, increased survival rate, increased growth rate, increased height, increased chlorophyll content and/or increased yield (e.g., increased biomass, increased seed yield, increased grain yield at standard moisture percentage, increases shoot length, decreased electrolyte leakage, increased grain weight per plot, increased percent yield recovery, decreased yield reduction, and/or decreased percent barren) when grown under abiotic stress conditions. A plant or plant part that exhibits enhanced abiotic stress tolerance may be designated as "abiotic stress tolerant."

As used herein, the term "enhanced drought tolerance" refers to an improvement in one or more water optimization traits as compared to one or more controls (e.g., a native plant/plant part of the same species). A plant or plant part that exhibits decreased water loss, decreased accumulation of one or more reactive oxygen species, decreased accumulation of one or more salts, increased salt excretion, increased accumulation of one or more dehydrins, improved root architecture, improved osmotic pressure regulation, increased accumulation of one or more late embryogenesis abundant proteins, increased survival rate, increased growth rate, increased height, increased chlorophyll content and/or increased yield as described above, as compared to a control plant (e.g., an untreated plant) when each is grown under the same drought stress conditions displays enhanced drought tolerance and may be designated as "drought tolerant." In some embodiments, the plant or plant part exhibits an increased survival rate after being subjected to drought stress conditions (e.g., incubation in a 200 g/L PEG6000 solution).

As used herein, the term "enhanced osmotic stress tolerance" refers to an improvement in one or more osmotic pressure optimization traits as compared to one or more controls (e.g., a native plant/plant part of the same species). A plant or plant part that exhibits decreased water loss, decreased accumulation of one or more reactive oxygen species, decreased accumulation of one or more salts, increased salt excretion, increased accumulation of one or more dehydrins, improved root architecture, improved osmotic pressure regulation, increased accumulation of one or more late embryogenesis abundant proteins, increased survival rate, increased growth rate, increased height, increased chlorophyll content and/or increased yield as described above, (as compared to a control plant (e.g., untreated plant) when each is grown under the same osmotic stress conditions) displays enhanced osmotic stress tolerance and may be designated as "osmotic stress tolerant." In some embodiments, the plant or plant part exhibits an increased survival rate after being subjected to mannitol-induced osmotic stress conditions. (e.g., incubation in a 200 mM mannitol solution).

As used herein, the term "enhanced salt stress tolerance" refers to an improvement in one or more salt optimization traits as compared to one or more controls (e.g., untreated plant). A plant or plant part that exhibits decreased water loss, decreased accumulation of one or more reactive oxygen species, decreased accumulation of one or more salts, increased salt excretion, increased accumulation of one or more dehydrins, improved root architecture, improved osmotic pressure regulation, increased accumulation of one or more late embryogenesis abundant proteins, increased survival rate, increased growth rate, increased height, increased chlorophyll content and/or increased yield as described above, as compared to a control plant (e.g., an untreated plant) when each is grown under the same salt stress conditions displays enhanced salt stress tolerance and may be designated as "salt stress tolerant."

As used herein, the term "enhanced temperature stress tolerance" refers to an improvement in one or more temperature tolerance traits as compared to one or more controls (e.g., an untreated plant). A plant or plant part that exhibits decreased water loss, decreased accumulation of one or more reactive oxygen species, decreased accumulation of one or more salts, increased salt excretion, increased accumulation of one or more dehydrins, improved root architecture, improved osmotic pressure regulation, increased accumulation of one or more late embryogenesis abundant proteins, increased survival rate, increased growth rate, increased height, increased biomass, increased chlorophyll content, increased grain yield as described above, as compared to a control plant (e.g., an untreated plant) when each is grown under the same temperature stress conditions displays enhanced temperature stress tolerance and may be designated as "temperature stress tolerant."

It is to be understood that "drought tolerant," "osmotic stress tolerant," "salt stress tolerant," and "temperature stress tolerant" plants and plant parts may also be referred to as a "abiotic stress tolerant" because drought stress, osmotic stress, salt stress and temperature stress are all abiotic stresses.

As used herein, the term "plant" may refer to any suitable plant, including, but not limited to, spermatophytes (e.g., angiosperms and gymnosperms) and embryophytes (e.g., bryophytes, ferns and fern allies). In some embodiments, the plant is a monocotyledonous (monocot) plant such as a rice, maize, wheat, barley, sorghum, millet, oat, triticale, rye, buckwheat, fonio, quinoa, sugar cane, bamboo, banana, ginger, onion, lily, daffodil, iris, amaryllis, orchid, canna, bluebell, tulip, garlic, secale, einkorn, spelt, emmer, durum, kamut, grasses, teff, milo, flax, *Tripsacum* sp., or teosinte plant. In some embodiments, the plant is a dicotyledonous (dicot) plant such as a blackberry, raspberry, strawberry, barberry, bearberry, blueberry, coffee berry, cranberry, crowberry, currant, elderberry, gooseberry, goji berry, honeyberry, lemon, lime, lingonberry, mangosteen, orange, pepper, persimmon, pomegranate, prune, cotton, clover, acai, plum, peach, nectarin, cherry, guava, almond, pecan, walnut, amaranth, apple, sweet pea, pear, potato, soybean, sugar beet, sunflower, sweet potato, tamarind, tea, tobacco or tomato plant.

As used herein, the term "plant cell" refers to a cell existing in, taken from and/or derived from a plant (e.g., a cell derived from a plant cell/tissue culture). Thus, the term "plant cell" may refer to an isolated plant cell, a plant cell in a culture, a plant cell in an isolated tissue/organ and/or a plant cell in a whole plant.

The term "plant part" refers to at least a fragment of a whole plant or to a cell culture or tissue culture derived from a plant. Thus, the term "plant part" may refer to plant cells, plant tissues and plant organs, as well as cell/tissue cultures derived from plant cells, plant tissues and plant cultures. Embodiments of the present invention may comprise and/or make use of any suitable plant part, including, but not limited to, anthers, branches, buds, calli, clumps, cobs, cotyledons, ears, embryos, filaments, flowers, fruits, husks, kernels, leaves, lodicules, ovaries, palea, panicles, pedicels, pods, pollen, protoplasts, roots, root tips, seeds, silks, stalks, stems, stigma, styles, and tassels. In some embodiments, the plant part is a plant germplasm.

A "cell protectant" is used to describe a substance that confers stability to cell membrane and therefore to the whole cell. With it, the biofertilizer keeps a cell density about $1 \times 10^9$ CFU/mL at least, for 8 months, thus increasing its storage life. Such a cell protectant can include, but is not limited to sodium alginate, gum arabic, polyvinylpyrrolidone, polyethyleneglycol, trehalose, glycerol, high-density carboxymethylcellulose, polysorbate 20 or a mixture of multiple protectants. In an even more preferable mode of the present invention, the cell protectant is added in a final concentration of 0.1 to 2.5% of the vehicle.

As used herein, a "carrier-based formulation" for the bacteria containing compositions refers to carriers which include, but are not limited to peat, charcoal, soil mixture, vermiculite, perlite, bentonite, compost, agro-industrial residues, clays, or urea-formaldehyde polymers.

"Solvent-based formulations" refer to solvents including alkanolamines such as triethanolamine, diethanolamine, monoethanolamine; alkyldiethanolamines, dialkylmonoethanolamines, wherein the alkyl group is $C_1$-$C_{24}$ branched or unbranched alkyl chain; dimethylsulfoxide (DMSO); alkylsulfones such as sulfolane {2,3,4,5-tetrahydrothiophene-1,1-dioxide); alkyl amides such as N-methylpyrrolidone, M-ethylpyrrolidone, or dimethylformamide; monoalcohols such as methanol, ethanol, propanol, isopropanol, or benzyl alcohol; glycols such as ethylene glycol, propylene glycol, diethylene glycol, or dipropylene glycol; glycol derivatives and protected glycols; glycerol and glycerol derivatives (trialcohols) including protected glycerols such as isopropylidine glycerol; dibasic esters and derivatives thereof; alkylene carbonates such as ethylene carbonate or propylene carbonate; monobasic esters such as ethyl lactate or ethyl acetate; polymers of carboxylic acids such as maleic acid, oleic acid, itaconic acid, acrylic acid, or methacrylic acid; monoalkyl glycol ethers and dialkyl glycol ethers; glycol esters; surfactants such as alkylbenzenesulfonates, lignin sulfonates, alkylphenol ethoxylates, or polyethoxylated amines.

The phrase "Encapsulated formulations" refers to one or more bacterial strains encapsulated in, for example, a suitable polymeric matrix. In one example, encapsulation may comprise alginate beads such as has been described by Young et al, 2006, Encapsulation of plant growth-promoting bacteria in alginate beads enriched with humid acid, Biotechnology and Bioengineering 95:76-83. Those skilled in the art will appreciate that any suitable encapsulation material or matrix may be used. Encapsulation may be achieved using methods and techniques known to those skilled in the art. Encapsulated microorganisms can include nutrients or other components of the inoculant or fertilizer composition in addition to the microorganisms.

The term "improving soil quality" refers to the increasing the amount and/or availability of nutrients required by, or beneficial to plants, for growth. For example, such nutrients include, without limitation, nitrogen, phosphorous, potassium, copper, zinc, boron and molybdenum. Also encompassed by the term "improving soil quality" is reducing or minimizing the amount of an element that may be detrimental to plant growth or development such as, for example iron and manganese. Thus, improving soil quality by use of microbial inoculants and fertilizer compositions of the present disclosure thereby assists and promotes the growth of plants in the soil.

The term "effective amount" refers to an amount of microbial inoculant or fertilizer composition applied to a given area of soil or vegetation that is sufficient to promote one or more beneficial or desired outcomes, for example, in terms of plant growth rates, crop yields, or nutrient availability in the soil. An "effective amount" can be provided in one or more administrations. The exact amount required will vary depending on factors such as the identity and number of individual strains employed, the plant species being treated, the nature and condition of the soil to be treated, the exact nature of the microbial inoculant or fertilizer composition to be applied, the form in which the inoculant or fertilizer is applied and the means by which it is applied, and the stage of the plant growing season during which application takes place. For any given case, an appropriate "effective amount" may be determined by one with ordinary skill in the art using only routine experimentation.

As used herein, the term "contacting" in the context of contacting a plant with a bacteria, or a product thereof, refers to any suitable method for bringing a bacteria containing composition or formulation, or a product thereof, in contact with the plant. Such methods include, but are not limited to, dipping, dripping, spraying, root dipping, soil drenching, dabbing, painting, coating, blotting, fumigating, irrigating, atomizing, or soil injection. Contacting can refer to application to the plant directly. For example, a plant can be dipped or otherwise contacted with one or more bacteria or products thereof. The contacting can be performed prior to planting of the plant, after the planting of the plant, or during transfer of a plant from one planting media to another. Alternatively, the contacting can be applied to the plant or seed indirectly. For example, a soil or other planting media can be contacted with one or more bacteria or products thereof, and the plant contacted with the soil or other planting media. The bacteria or products thereof can be in a liquid (e.g., a solution or suspension) or solid form. Exemplary solid forms include but are not limited to a powder or a paste. The bacteria can be in an otherwise sterile carrier or medium. The medium can be liquid (e.g., a solution or suspension of bacteria) or solid (e.g., a powder or paste).

Compositions of the present invention may include formulation inerts added to compositions comprising cells, cell-free preparations or metabolites to improve efficacy, stability, or usability and/or to facilitate processing, packaging or end-use application. Such formulation inerts and ingredients may include carriers, stabilization agents, nutrients, or physical property modifying agents, which may be added individually or in combination. In some embodiments, the carriers may include liquid materials such as water, oil, and other organic or inorganic solvents and solid materials such as minerals, polymers, or polymer complexes derived biologically or by chemical synthesis. In some embodiments, the carrier is a binder or adhesive that facilitates adherence of the composition to a plant part, such as a seed or root. See, for example, Taylor, A. G., et al., "Concepts and Technologies of Selected Seed Treatments", Anna. ev. Phytopathol. 28: 321-339 (1990). The stabilization agents may include anti-caking agents, anti-oxidation agents, desiccants, protectants or preservatives. The nutrients may include carbon, nitrogen, or phosphorous sources such as sugars, polysaccharides, oil, proteins, amino acids, humic acids, hormones, plant growth regulators, fatty acids or phosphates. The physical property modifiers may include bulking agents, wetting agents, thickeners, pH modifiers, rheology modifiers, dispersants, adjuvants, surfactants, sun screening agents, antifreeze agents or colorants. In some embodiments, the composition comprising cells, cell-free preparations or metabolites produced by fermentation can be used directly with or without water as the diluent without any other formulation preparation. In some embodiments, the formulation inerts are added after concentrating fermentation broth and during and/or after drying.

The plant growth promoting bacterial agents can be applied in combination with synthetic chemicals, such as pesticides, nematicides, miticides, or fungicides. In some cases, a biocontrol agent containing *P. aspalathi* WSF14 and/or *P. aspalathi* WSF23 or a product thereof can be mixed with one or more other chemical and non-chemical additives, adjuvants or treatments, wherein such treatments include but are not limited to chemical and non-chemical fungicides, insecticides, miticides, nematicides, fertilizers, nutrients, minerals, auxins, growth stimulants and the like. In some cases, the plant growth promoting bacterial agent(s) allows the use of a lower amount of synthetic chemical to obtain the same degree of abiotic stress or pest tolerance.

Methods of Application

Compositions or formulations as described above can be applied to a plant to increase abiotic stress resistance in plants and plant parts. In some cases, the composition as described above can be applied to a plant to increase the overall plant health. The term "plant health" generally refers various aspects of plant growth or resistance to external insults. For example, a plant with increased plant health may exhibit one or more of the following improved crop characteristics including: emergence, crop yields, protein content, oil content, starch content, more developed root system, improved root growth, improved root size maintenance, improved root effectiveness, improved stress tolerance (e.g., against drought, heat, salt, UV, water, cold), reduced ethylene (reduced production and/or inhibition of reception), tillering increase, increase in plant height, bigger leaf blade, less dead basal leaves, stronger tillers, greener leaf color, pigment content, photosynthetic activity, less input needed (such as fertilizers or water), less seeds needed, more productive tillers, earlier flowering, early grain maturity, less plant verse (e.g., less lodging), increased shoot growth, enhanced plant vigor, increased plant stand, and early and better germination.

The effect of a composition according to the present invention on plant health as defined herein can be determined by comparing plants which are grown under the same environmental conditions, whereby a part of said plants is treated with a composition as described herein and another part of said plants is not treated with a composition according to the present invention. In some cases, said other part is not treated at all, treated with a placebo (e.g., an application without a composition according to the invention. In some cases, said other part is treated with a conventional treatment with a known efficacy.

A composition according to the present invention can be applied in any desired manner, such as in the form of a seed coating, soil drench, and/or directly in-furrow and/or as a foliar spray and applied either pre-emergence, post-emergence or both. The composition can be applied to the seed, the plant, harvested fruits and vegetables, or the planting media (e.g., soil) wherein the plant is growing or wherein it is desired to grow. In some cases, the composition is applied during, before, or shortly after, transfer of the plant from one planting media to another. For example, a plant may be grown in a greenhouse until it reaches a certain stage, harvested, treated, and transferred to a field. A composition described herein can be applied to a conventional or transgenic plant.

In some embodiments, a composition containing at least one plant growth promoting strain described herein or a product thereof can be contacted with a plant and simultaneously or sequentially a composition containing a second bacterial strain can be contacted with the plant. The contacting can be performed by a wide variety of methods known in the art.

In some cases, the plant is contacted with a formulation containing the growth promoting bacterial strain(s) formulated into a single, stable composition with an agriculturally acceptable shelf life. In some cases, one or more compositions or components are combined before, or at the time of use. In some cases, a formulation is in a single "ready-mix" form. In some cases, the formulation is a combined spray mixture composed from solo-formulations that are combined during the application process, such as in a "tank mix" formulation. In some case, one or more components of the composition are combined when they are contacted with a plant in a sequential manner, i.e., one after the other within a reasonably short period, such as a few hours or days, e.g., 0.5, 1, or 2 hours to 7 days. The order of applying the composition according to the present invention is not essential for working the present invention.

Contacting a plant with the compositions and formulations described herein can be performed using a wide variety of customary treatment methods. For example the plant can be contacted by dipping, coating, seed coating, spraying, atomizing, irrigating, evaporating, dusting, fogging, broadcasting, foaming, painting, spreading-on, watering (drenching), soil injection, or drip irrigating.

The amount of composition or formulation that is contacted with the plant depends on the final formulation, the size or type of the plant, plant parts, seeds, harvested fruits and vegetables to be treated. In one embodiment a composition is contacted with a plant, the composition containing one or more strains of P. aspalathi at a concentration of at least $10^5$ colony forming units per gram preparation, such as $10^5$-$10^{12}$ cfu/g, $10^6$-$10^{11}$ cfu/g, $10^7$-$10^{10}$ cfu/g, or $10^9$-$10^{10}$ cfu/g at the time point of applying the bacterial plant growth promoting agents on a plant or plant parts such as seeds, fruits or vegetables.

The different P. aspalathi strains, can be used or employed in a synergistic ratio (e.g., by weight, mass, colony forming units, or cells per unit volume). The synergistic ratios can be determined using routine methods. These ratios can refer to the ratio within a combined-formulation as well as to the ratio when both components are applied as mono-formulations to a plant to be treated.

In one embodiment of the present invention, the concentration of one or more P. aspalathi strains after dispersal is at least 50 g/ha, such as 50-7500 g/ha, 50-2500 g/ha, 50-1500 g/ha; at least 250 g/ha, at least 500 g/ha or at least 800 g/ha. The application rate of composition to be employed or used according to the present invention may vary. The skilled person is able to find the appropriate application rate by way of routine experiments.

In some embodiments, one or more compositions of the present invention are contacted with a plant by applying the composition to a seed. In some cases, the seed is contacted with one or more P. aspalathi strains or a product thereof. In some cases, one or more individual compositions, or components, of the invention may be present in different layers on the seed. In some cases, following treatment with the composition of the invention, the seed is subjected to a film-coating process in order to prevent dust abrasion of the seed.

A composition as described herein can be applied alone or in a suitable formulation to the seed. The seed can be treated in a condition such that no damage occurs in the course of the treatment. Generally speaking, the seed may be treated at any point in time between harvesting and sowing. Typically, the seed is used which has been separated from the plant and has had cobs, hulls, stems, husks, hair or pulp removed. Thus, for example, the seed or seeds may be used that have been harvested, cleaned and dried to a moisture content of less than 15% by weight. Alternatively, seed can also be used that after drying has been treated with water, for example, and then dried again.

When treating the seed it is necessary, generally speaking, to ensure that the amount of the composition of the invention, and/or of other additives, that is applied to the seed is selected such that the germination of the seed is not adversely affected, and/or that the plant which emerges from the seed is not damaged. This is the case in particular with active ingredients which may exhibit phytotoxic effects at certain application rates.

The compositions of the invention can be applied in the form of a suitable formulation to the seed. Suitable formulations and methods for seed treatment are known to the skilled person and are described in, for example, the following documents; U.S. Pat. Nos. 4,272,417; 4,245,432; 4,808,430; 5,876,739; US 2003/0176428; WO 2002/080675; or WO 2002/0281 86, the contents of which are hereby incorporated in their entirety for all purposes.

Lyophilization Procedure

Freeze drying bacteria (lyophilization) is a very well-established method for the archiving and long-term storage. Initial reports of freeze-drying bacteria can be found in the middle of last century. The approaches used vary widely, but they all follow the standard process associated with lyophilization, namely, freezing of the sample, application of a high vacuum, warming of the sample while under vacuum which causes water sublimation, driving off excess water through a drying phase, and, finally, sealing of the sample to prevent water uptake. This general process is used to preserve bacteria, fungi, yeasts, proteins, nucleic acids, and any other molecules which may be degraded due to the presence of water.

Thus, in one aspect of the invention, one or more of the bacteria will be applied to a plant or a plant part (such as seeds) as a lyophilized (freeze-dried) powder. In brief, the liquid culture will be: centrifuged, re-suspended in a lyophilization medium which will optionally include cryoprotectants and biological- and/or chemical-oxygen scavengers, transferred to a shelf lyophilizer, lyophilized, and packaged for transport and storage.

In an alternative approach, one or more bacteria may be encapsulated in alginate beads enriched with humic acid as described by Young C C et al., Biotechnol Bioeng. 2006 Sep. 5; 95(1):76-83. Also see "Alginate beads as a storage, delivery and containment system for genetically modified PCB degrader and PCB biosensor derivatives of *Pseudomonas fluorescens* F113 B" by Power et al., Journal of Applied Microbiology 110, 1351-1358, 2011.

The carrier and bacteria, for example, (with or without additives) can be applied to seeds of cotton crops using a commercial seed dressing machine (e.g., MAYJOY High Speed Seeds Dressing Machine/Corn Seed Dresser).

In some embodiments, bacteria described herein may also be used as an additive to create seed balls. In this approach, clay mixed with freeze-dried preparation of an bacteria and seeds (2-3, 4-5, 7-10, 15-20 or any suitable amount) are added to the center of a small clay ball. The seed balls are then dried and stored for future use. In some embodiments, the plant element is associated with a single strain or a plurality of strains on its surface. Such association is contemplated to be via a mechanism selected from the group consisting of: spraying, immersion, coating, encapsulating, dusting, dripping, aerosolizing, seed treatment, root wash, seedling soak, foliar application, soil inocula, in-furrow application, sidedress application, soil pre-treatment, wound inoculation, drip tape irrigation, vector-mediation via a pollinator, injection, osmopriming, hydroponics, aquaponics, and aeroponics.

Any of the bacteria described herein can also be applied to host plants in soil drenching approaches. For example, freeze dried preparation of *aspalathi* can be mixed with a liquid carrier (comprising water, buffers, plant nutrients, and microbial nutrients). This liquid preparation of bacterium and carrier (with additives) may be applied to the soil around plant or seed or in the alternative be applied to soil and plants using a commercial sprayer.

The following materials and methods are provided to facilitate the practice of the embodiments.

Bacterial Preparation and Inoculation

Bacterial cultures were revived from frozen stock vials stored at −80° C. by streaking on nutrient agar plates. Single colonies were picked and inoculated in Luria broth and incubated at 23° C. on a water-bath shaker for 48 h. Bacterial suspensions were centrifuged at 8000 g for 10 min at 4° C. then re-suspended in deionized water. The centrifuge and re-suspension process was repeated twice to remove the Luria broth. The prepared bacterial suspension was adjusted to optical density of 1.0. Plants were inoculated by soil drenching with the prepared bacterial inoculum into each pot twice at an interval of 24 h (50 mL for tomatoes and creeping bentgrass; 200 mL for maize). The control groups for the bacterial inoculation treatments were watered with an equivalent amount of deionized water.

Physiological Analyses

Turf quality was rated on a scale of 1 to 9, with 1 being brown and desiccated plants, 6 being the minimal acceptable level, and 9 being green and dense plants. Ratings were based on parameters such as uniformity, visual attractiveness, leaf color, and canopy density (Beard, 1972). This scale is known as the dark green color index (DGCI).

Leaf electrolyte leakage (EL) was measured as an indicator of cellular membrane stability according to the procedure by Blum and Ebercon (1981). Approximately 0.2 g fresh leaves were collected, rinsed with deionized water to remove exogenous solutes, and placed in a test tube containing 35 mL deionized water. Tubes were placed on a conical flask shaker for 16 h and the initial conductance ($C_i$) was measured using a conductivity meter (model 132; YSI, Yellow Springs, Ohio). Leaf samples were killed by autoclaving at 120° C. for 20 min and shaking for 16 h. The maximal conductance of killed tissue ($C_{max}$) was then measured. EL was calculated using the formula (%)=($C_i$/$C_{max}$)× 100.

Relative water content (RWC) was measured according to the procedure by Barrs and Weatherley (1962). Leaf RWC was calculated based on leaf fresh weight (FW), turgid weight (TW), and dry weight (DW) using the formula (%)=100×[(FW−DW)/(TW−DW)]. FW of leaves was determined with a mass balance immediately after detaching leaves from the plant. Samples were wrapped in tissue paper and submerged in deionized water for 24 h. Leaf samples were then removed from the water, blotted dry, and again weighed for TW. Following a drying period of 3 d at 80° C., samples were weighed a final time for DW.

Leaf photochemical efficiency was estimated by measuring chlorophyll fluorescence expressed as the ratio of variable to maximum fluorescence ($F_v/F_m$) with a fluorescence induction monitor (OS 1FL, Opti-Sciences, Hudson, N.H.). Leaves were dark adapted for 30 min before $F_v/F_m$ was measured.

Leaf chlorophyll content was quantified weekly according to the method described by Arnon (Arnon, 1949). Leaf tissue samples were obtained weekly from each pot and incubated in 10 mL dimethyl-sulfoxide in darkness for 24 hours to extract the chlorophyll from the tissue. The solution was then analyzed on a spectrophotometer (Spectronic Instruments, Inc., Rochester, N.Y.) at 663 and 645 nm. The tissue was then extracted from the solution and oven dried at 80° C. for 72 hours to obtain dry weights. Chlorophyll content was then calculated on a dry weight basis.

Root dry weights were measured at 14 d and 21 d of salinity treatment for tomato and at 28 d for corn. Roots were washed free of fritted clay and severed from shoots by destructively sampling. All tissues were dried at 80° C. for 3 d and their weights were measured using a mass balance. Root morphological parameters were analyzed upon severance from shoots. Roots were washed free of calcined clay and scanned with a digital scanner (Epson Expression 1680, U.S. Epson, Inc., Long Beach, Calif.) to generate high-definition digital images. Images were analyzed using WinRHIZO Basic V.2002 software (Regent Instruments Inc., Quebec, QC, Canada) for root length, volume, surface area, and diameter.

Ribosomal ITS DNA Sequences for these Strains:

```
WSF14 16S ribosomal RNA gene,
partial sequence (SEQ ID NO: 1)
AATTCCACGTGTAGCAGTGAAATGCGTAGAGATGT

GGAGGAATACCGATGGCGAAGGCAGCCCCCCTGGG

CCAATACTGACGCTCATGCACGAAAGCGTGGGGAG

CAAACAGGATTAGATACCCTGGTAGTCCACGCCCT

AAACGATGTCAACTAGTTGTTGGGGATTCATTTCC

TTAGTAACGTAGCTAACGCGTGAAGTTGACCGCCT

GGGGAGTACGGTCGCAAGATTAAAACTCAAAGGAA

TTGACGGGGACCCGCACAAGCGGTGGATGATGTGG
```

-continued

```
ATTAATTCGATGCAACGCGAAAAACCTTACCTACC

CTTGACATGTATGGAACCCTGCTGAGAGGTGGGGG

TGCCCGAAAGGGAGCCATAACACAGGTGCTGCATG

GCTGTCGTCAGCTCGTGTCGTGAGATGTTGGGTTA

AGTCCCGCAACGAGCGCAACCCTTGTCCCTAGTTG

CTACGCAAGAGCACTCTAGGGAGACTGCCGGTGAC

AAACCGGAGGAAGGTGGGGATGACGTCAAGTCCTC

ATGGCCCTTATGGGTAGGGCTTCACACGTCATACA

ATGGTCGGAACAGAGGGTCGCCAACCCGCGAGGGG

GAGCCAATCCCAGAAAACCGATCGTAGTCCGGATC

GCACTCTGCAACTCGAGTGCGTGAAGCTGGAATCG

CTAGTAATCGCGGATCAGCATGCCGCGGTGAATAC

GTTCCCGGGTCTTGTACACACCGCCCGTCACACCA

TGGGAGTGGGTTTTACCAGAAGTGGCTAGTCTAAC

CGCAAGGAGGA

WSF23 16S ribosomal RNA gene,
partial sequence (SEQ ID NO: 2):
GTAGCAGTGAAATGCGTAGAGATGTGGAGGGAATA

CCGATGGCGAAGGCAGCCCCCTGGGCCAATACTGA

CGCTCATGCACGAAAGCGTGGGGAGCAAACAGGAT

TAGATACCCTGGTAGTCCACGCCCTAAACGATGTC

AACTAGTTGTTGGGGATTCATTTCCTTAGTAACGT

AGCTAACGCGTGAAGTTGACCGCCTGGGGAGTACG

GTCGCAAGATTAAAACTCAAAGGAATTGACGGGGA

CCCGCACAAGCGGTGGATGATGTGGATTAATTCGA

TGCAACGCGAAAAACCTTACCTACCCTTGACATGT

ATGGAACCCTGCTGAGAGGTGGGGGTGCCCGAAAG

GGAGCCATAACACAGGTGCTGCATGGCTGTCGTCA

GCTCGTGTCGTGAGATGTTGGGTTAAGTCCCGCAA

CGAGCGCAACCCTTGTCCCTAGTTGCTACGCAAGA

GCACTCTAGGGAGACTGCCGGTGACAAACCGGAGG

AAGGTGGGGATGACGTCAAGTCCTCATGGCCCTTA

TGGGTAGGGCTTCACACGTCATACAATGGTCGGAA

CAGAGGGTCGCCAACCCGCGAGGGGGAGCCAATCC

CAGAAACCGATCGTAGTCCGGATCGCACTCTGCA

ACTCGAGTGCGTGAAGCTGGAATCGCTAGTAATCG

CGGATCAGCATGCCGCGGTGAATACGTTCCCGGGT

CTTGTACACACCGCCCGTCACACCATGGGAGTGGG

TTTTACCAGAAGTGGCTAGTCTAACCGCAAGGAGG

AC
```

The following examples are provided to illustrate certain embodiments of the invention. They are not intended to limit the invention in any way.

Example I

*Paraburkholderia* Strains and Methods of Use Thereof for Promoting Plant Growth

*P. aspalathi* WSF14

WSF14 was evaluated for its plant-growth-promoting properties and potential for horticultural and agricultural applications. Initial laboratory screening has indicated that WSF14 exhibits high ACC deaminase activity (1751 nmol/mg/h) and is able to produce significant quantities of the phytohormone auxin (98 ug IAA/mg).

Improved Drought Tolerance

Creeping bentgrass plants inoculated with WSF14 exhibited physiological and root growth properties characteristic of improved drought tolerance. Inoculated plants had improved turf quality, greater leaf water content, higher membrane stability, higher photochemical efficiency, greater chlorophyll content, and larger root diameter(s) compared to non-inoculated plants. FIGS. 1A-1F.

Improved Heat Tolerance

Figure 1A:
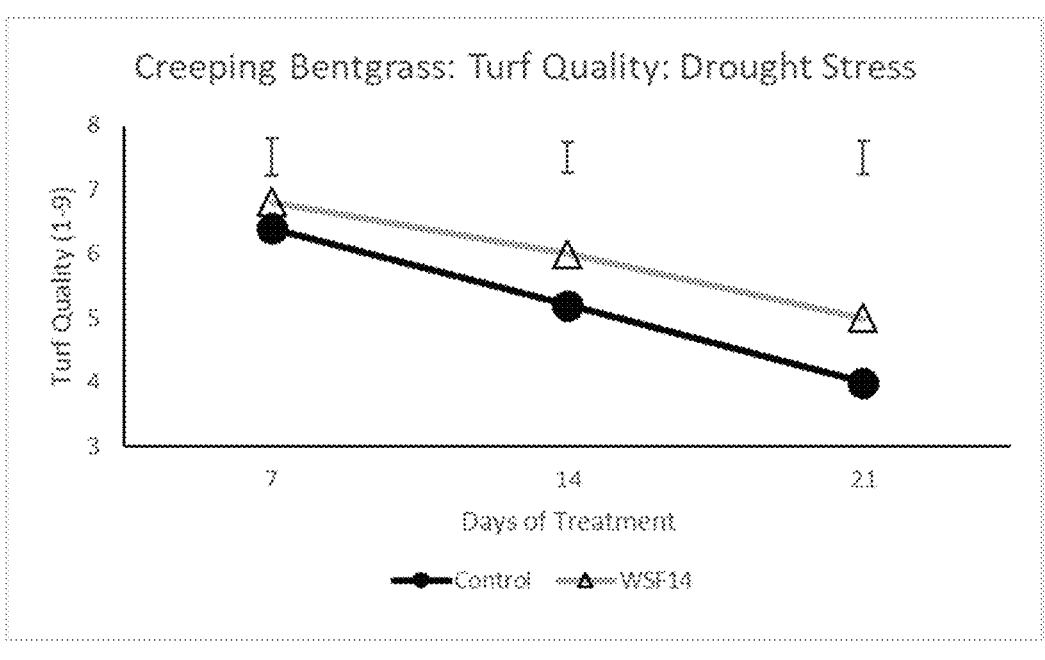
FIGS. 1A-1F. *P. aspalathi* WSF14 improves drought tolerance in creeping bentgrass plants.
Figure 1B:
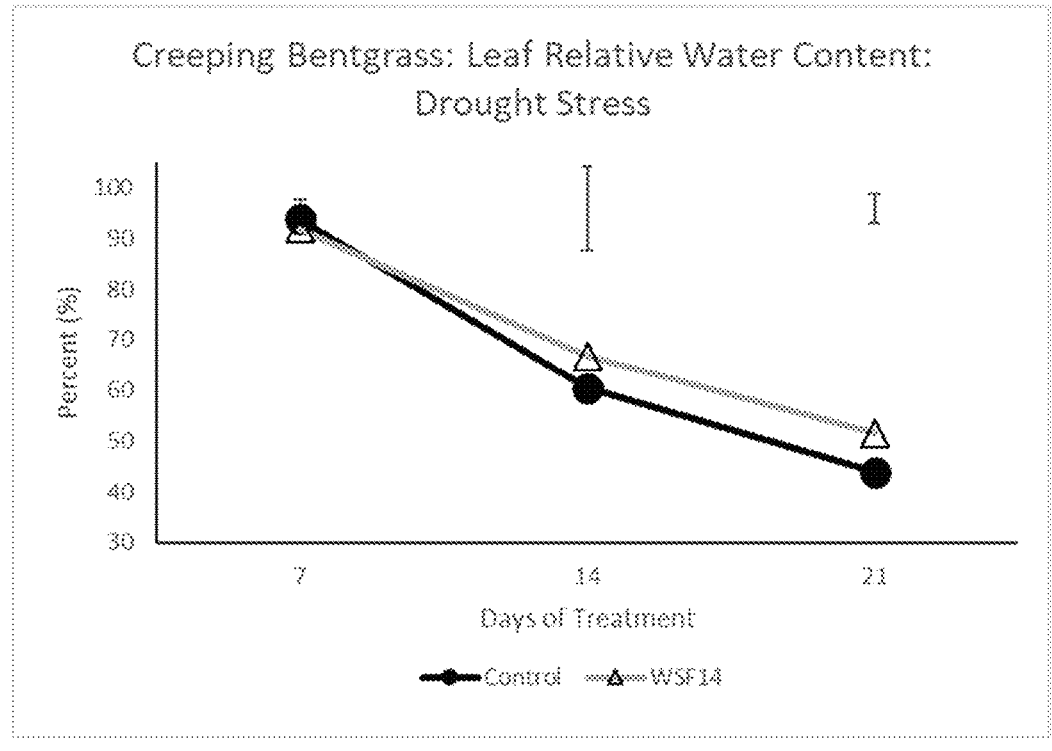
Figure 1C:
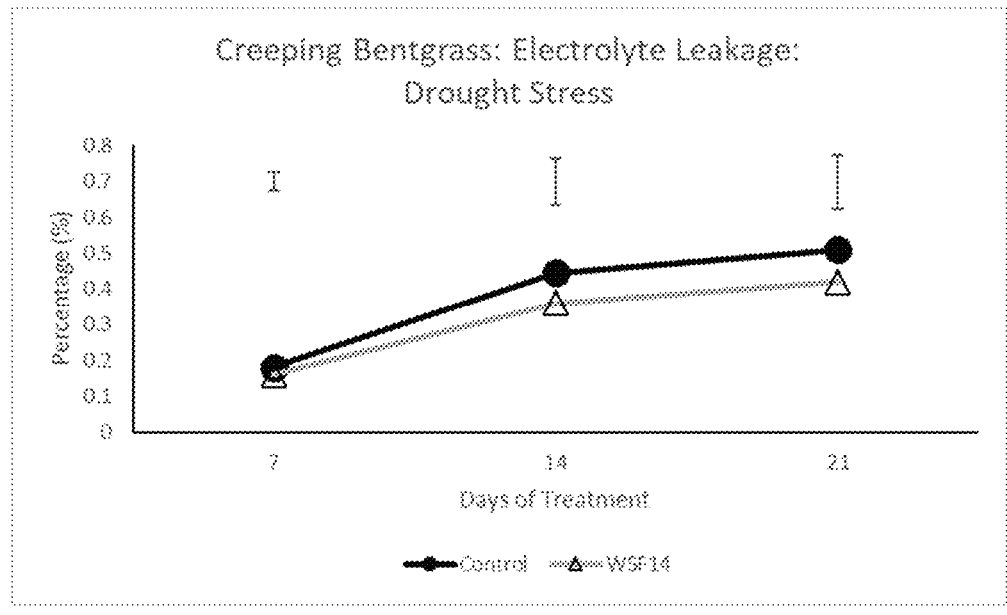
Figure 1D:
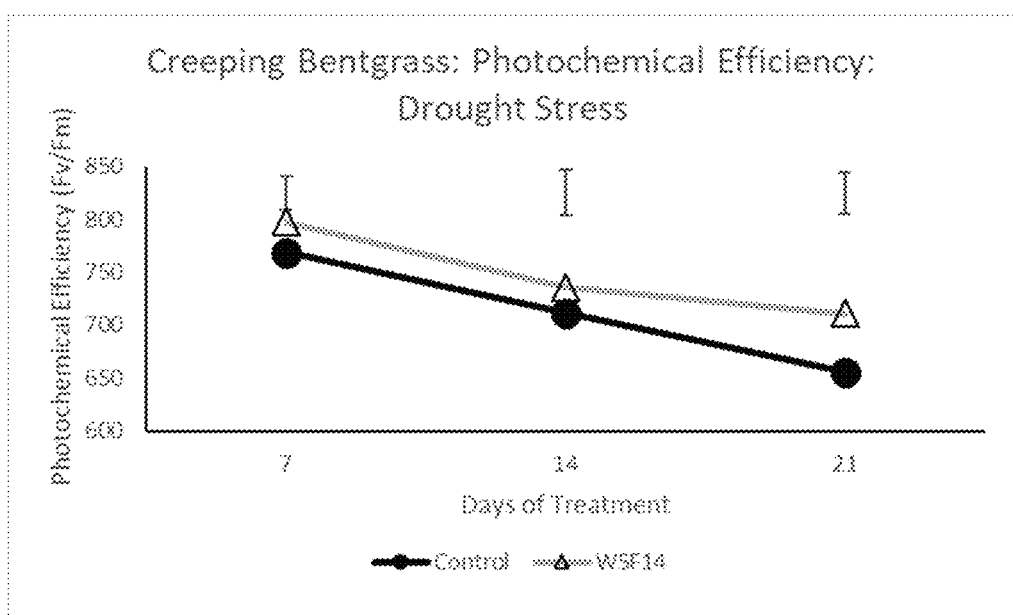
Figure 1E:
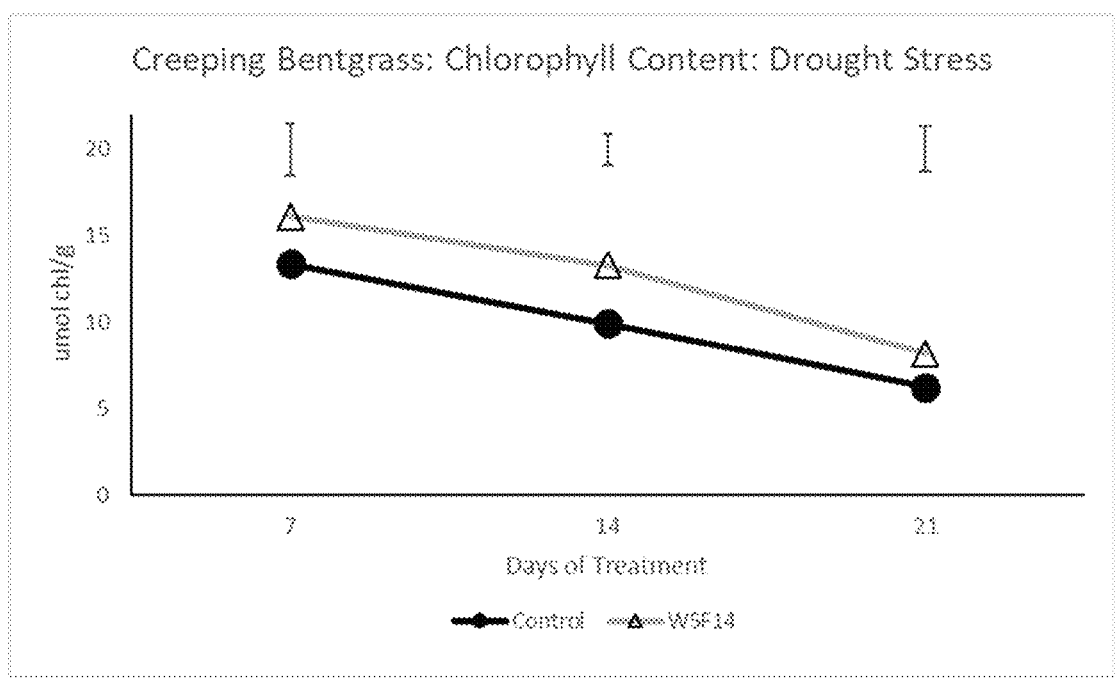
Figure 1F:
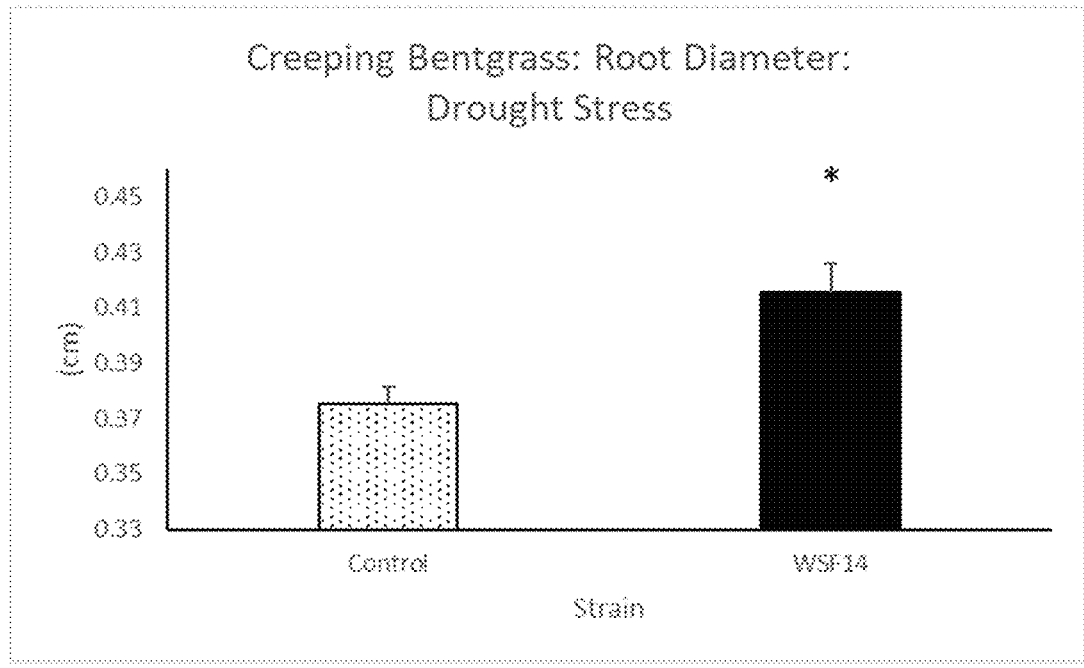
Figure 2A:
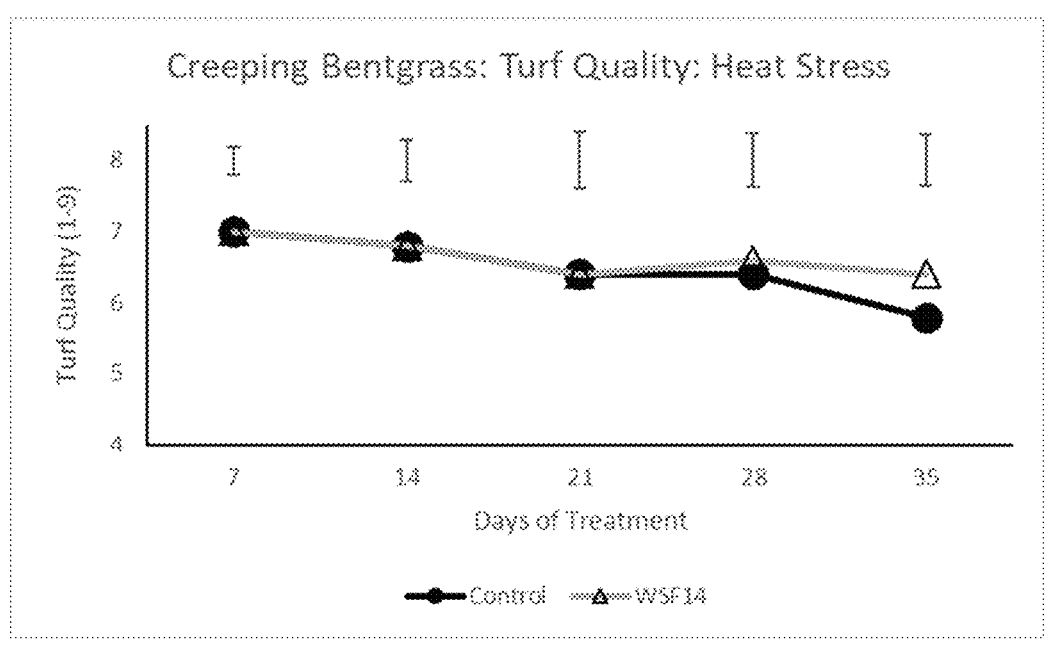
FIGS. 2A-2C. *P. aspalathi* WSF14 improves heat tolerance in creeping bentgrass plants.
Figure 2B:
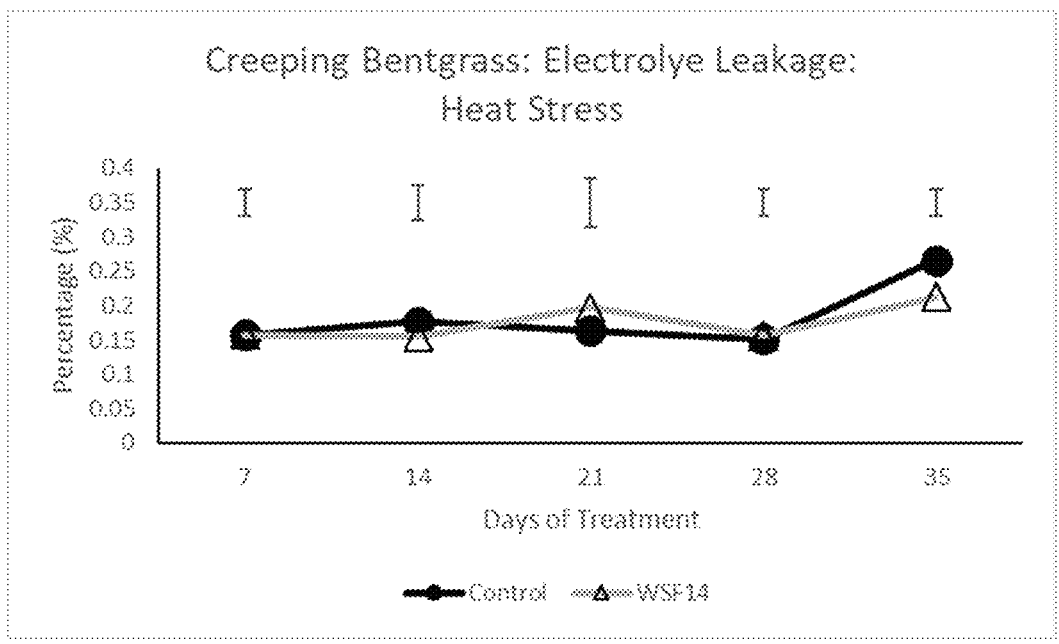
Figure 2C:
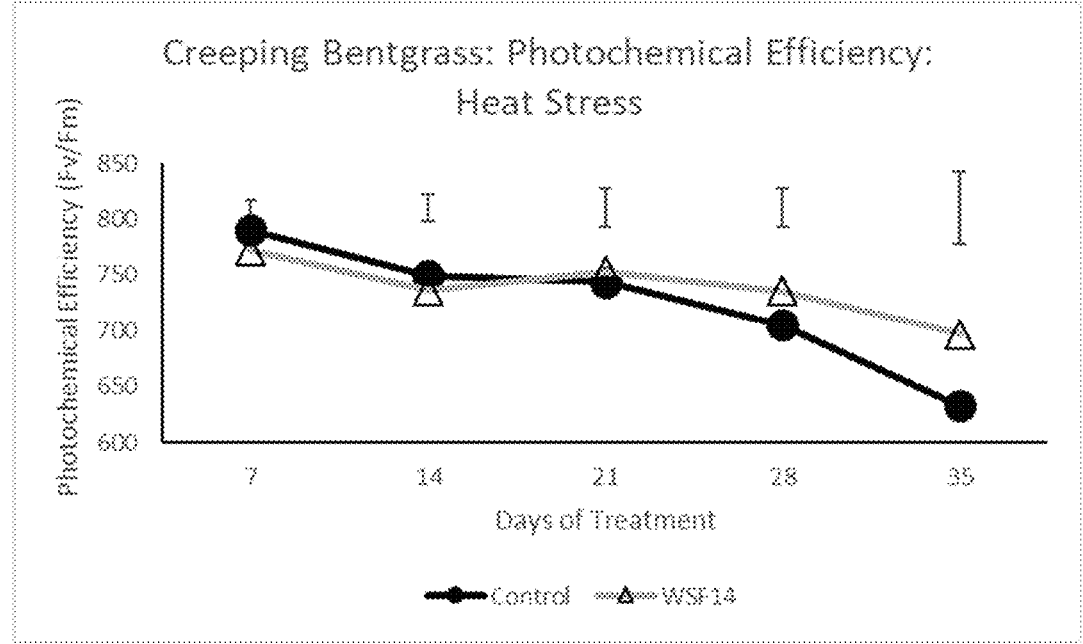

Creeping bentgrass plants inoculated with WSF14 exhibited physiological and root growth properties characteristic of improved heat tolerance. Inoculated plants had improved turf quality, higher membrane stability, and higher photochemical efficiency compared to non-inoculated plants. See FIGS. 2A-2C.

Example II

*P. aspalathi* WSF23

WSF23 was evaluated for its plant growth promoting properties and potential for horticultural and agricultural applications. Initial laboratory screening has indicated that WSF23 exhibits high ACC deaminase activity (1913 nmol/mg/h) and is able to produce significant quantities of the phytohormone auxin (93 ug IAA/mg).

Improved Salinity Tolerance and Low Fertility Tolerance

Figure 3A:
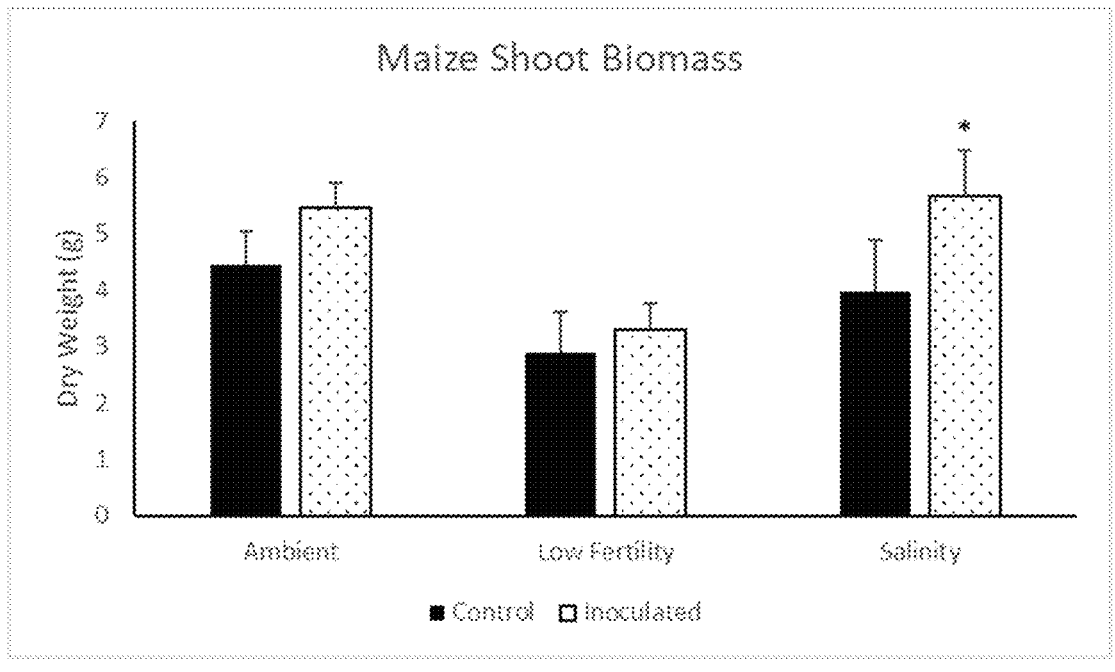
FIGS. 3A-3E. *P. aspalathi* WSF23 improves salinity tolerance and low fertility tolerance in maize plants.
Figure 3B:
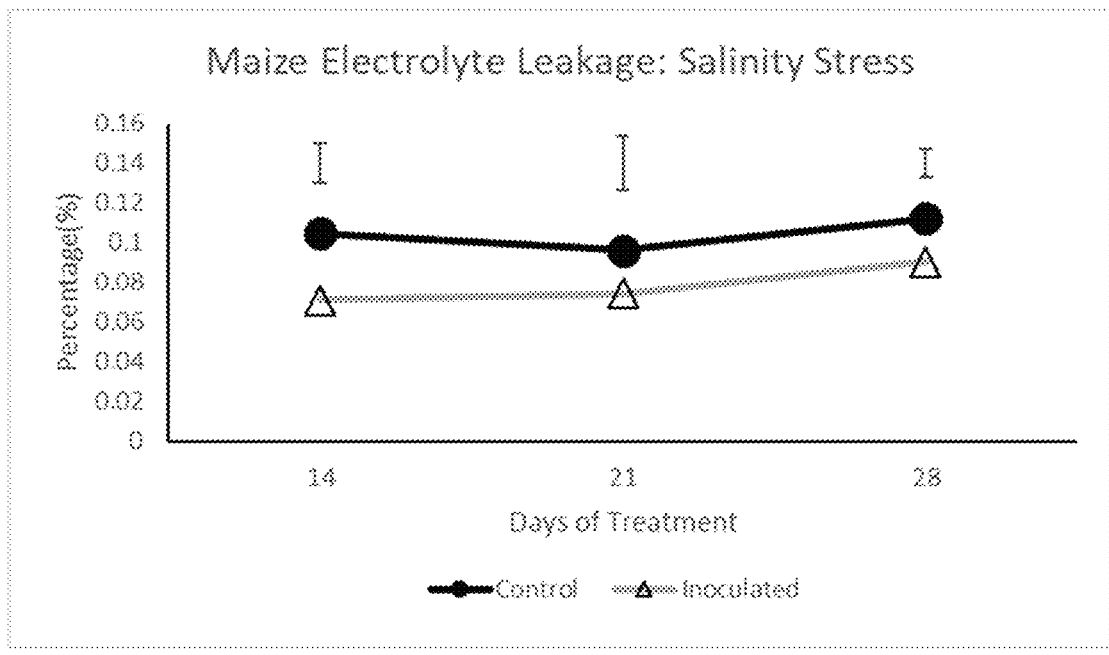
Figure 3C:
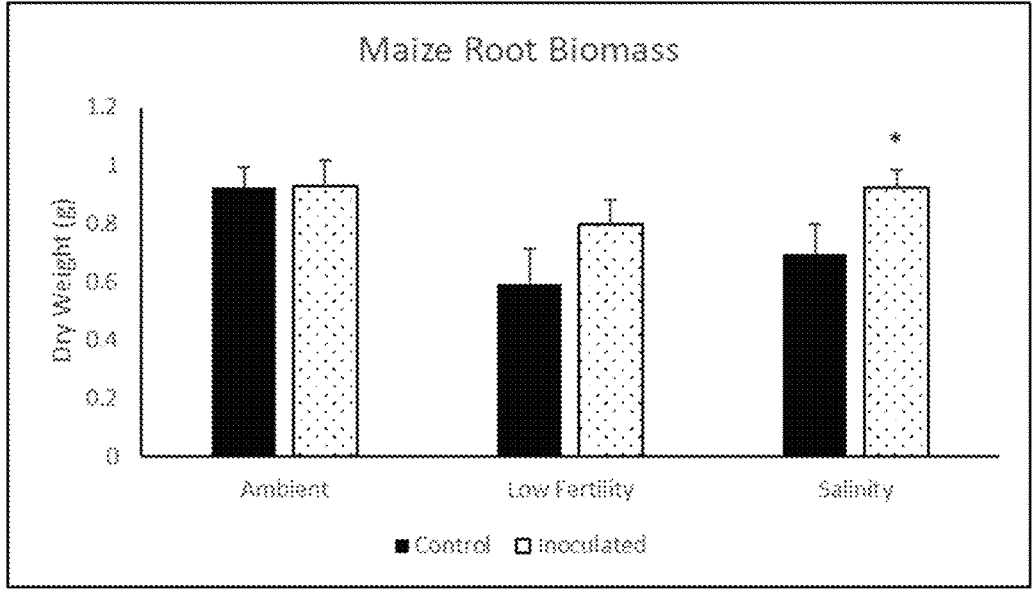
Figure 3D:
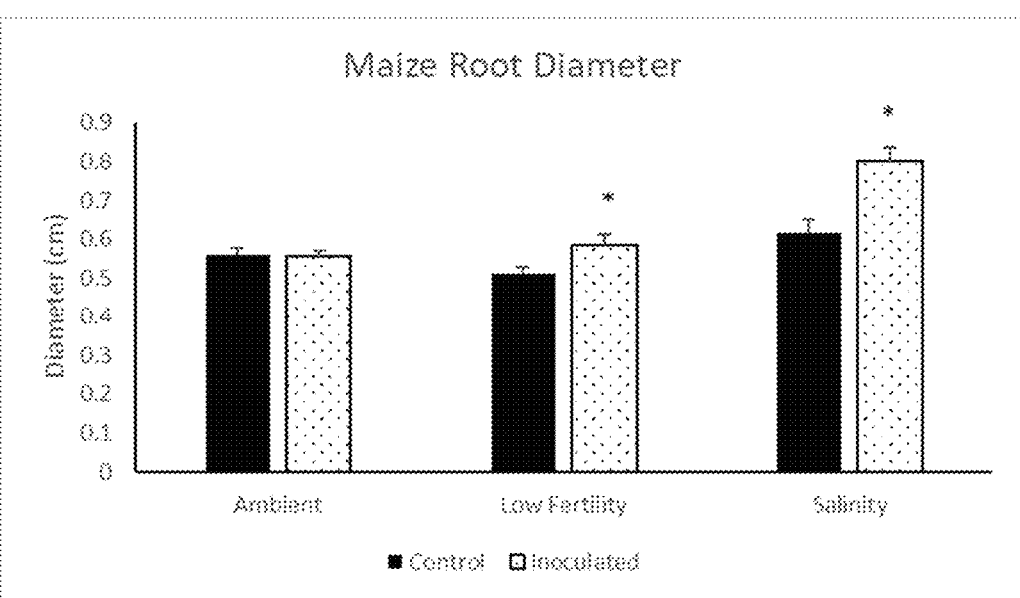
Figure 3E:
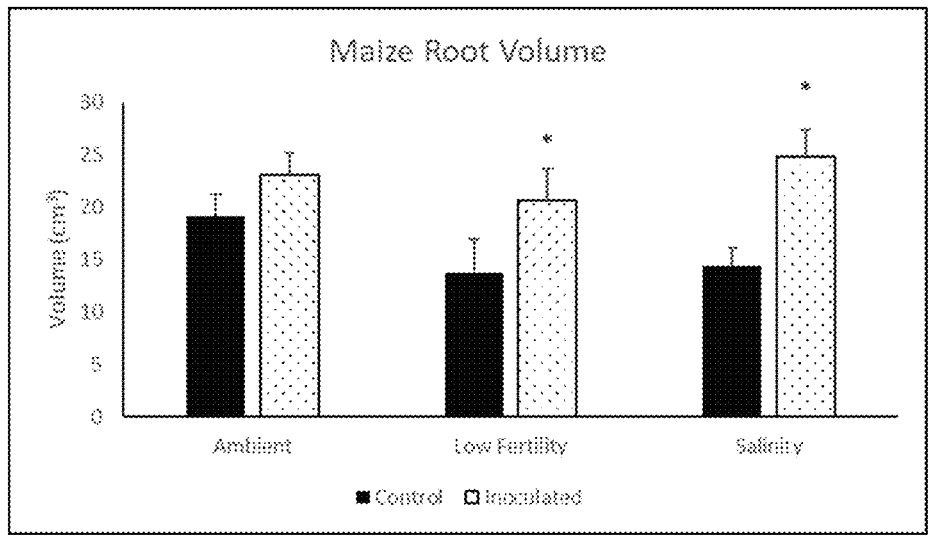

Maize inoculated with WSF23 exhibited physiological and shoot/root growth properties characteristic of improved salinity tolerance. Inoculated plants had reduced electrolyte leakage (FIG. 3B), increased shoot biomass (FIG. 3A), increased root biomass (FIG. 3C), larger root diameter(s) (FIG. 3D), and larger root volume (FIG. 3E) compared to non-inoculated plants.

Maize inoculated with WSF23 exhibited root growth properties characteristic of improved low-fertility tolerance. Inoculated plants had increased root diameter(s) and volume(s) (FIG. 3E) compared to non-inoculated plants.

Figure 4A:
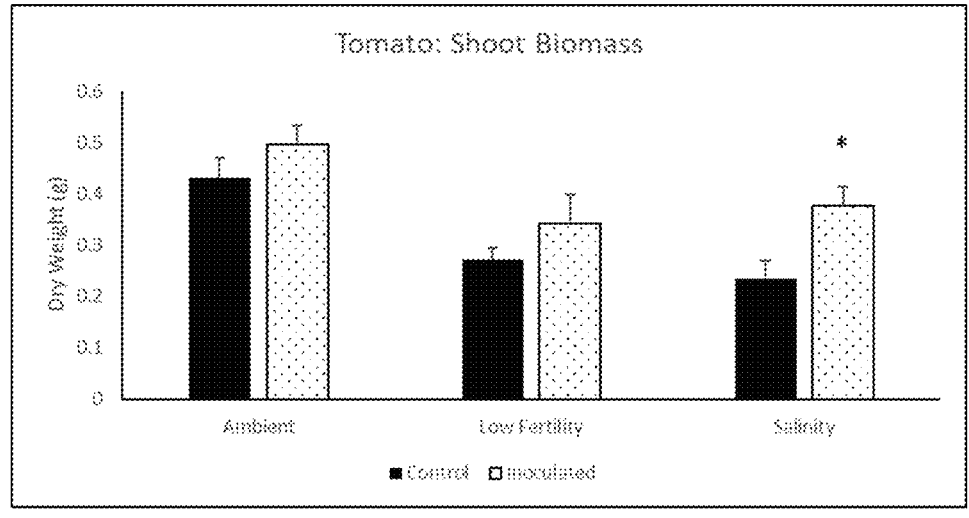
FIGS. 4A-4E. *P. aspalathi* WSF23 improves salinity tolerance and low fertility tolerance in tomato plants.
Figure 4B:
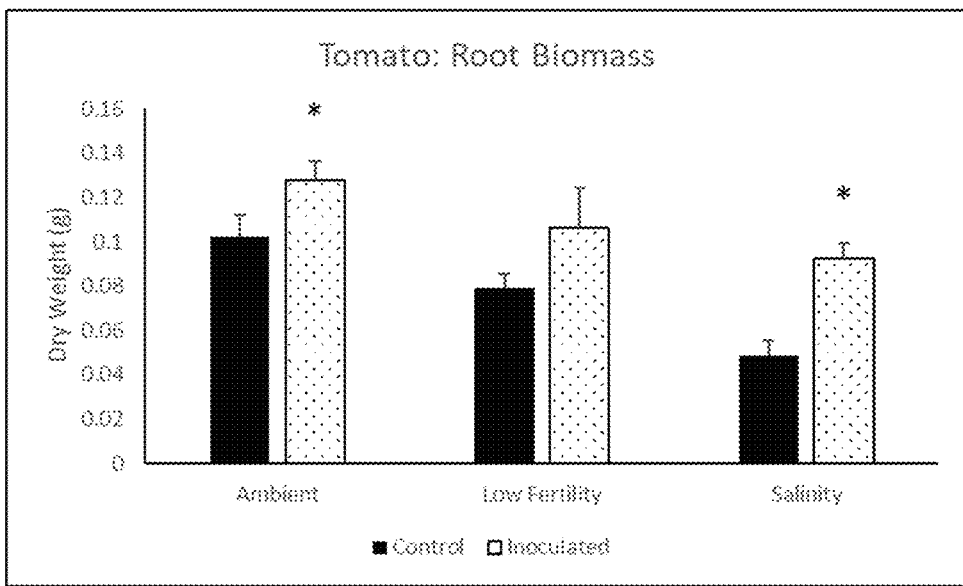
Figure 4C:
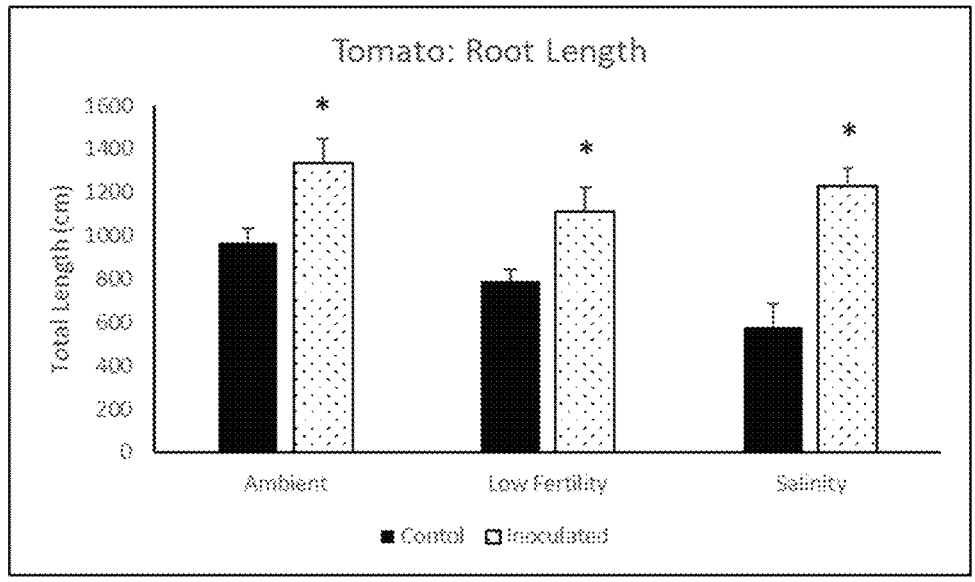
Figure 4D:
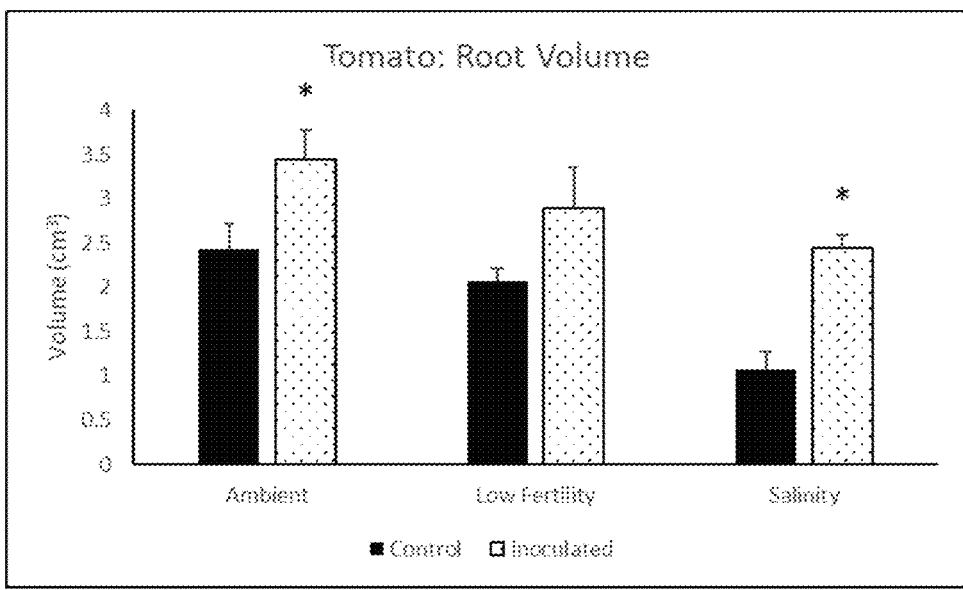
Figure 4E:
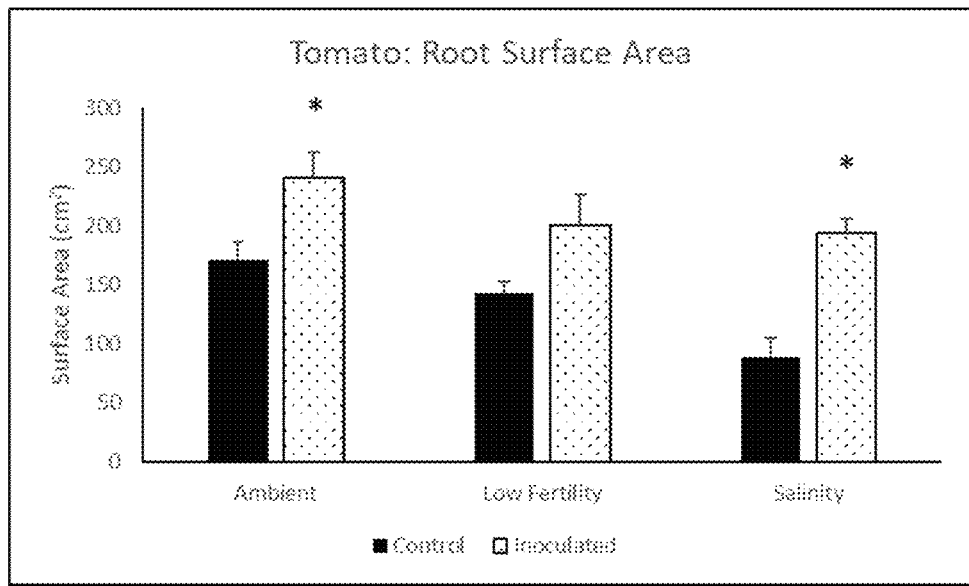

Tomato plants inoculated with WSF23 exhibited physiological and shoot/root growth properties characteristic of improved salinity tolerance. Inoculated plants had increased shoot biomass (FIG. 4A), increased root biomass (FIG. 4B), greater root length (FIG. 4C), larger root volume (FIG. 4D), and larger root surface area (FIG. 4E) compared to non-inoculated plants.

Tomato plants inoculated with WSF23 exhibited root growth properties characteristic of improved low-fertility tolerance. Inoculated plants had increased root length (FIG. 4C) compared to non-inoculated plants.

Improved Drought Tolerance and Post-Drought Recovery

Creeping bentgrass inoculated with WSF23 exhibited root growth properties characteristic of improved drought tolerance. Both inoculated and control plants were subjected to either 35 days of drought stress treatments or 35 days at optimum conditions. Turf quality, canopy density, DGCI (dark green color index), and tiller production were quantified during the 35-day period. ACC levels, soluble sugar levels, and root viability were quantified at the conclusion of the 35-day period.

Figure 5A:
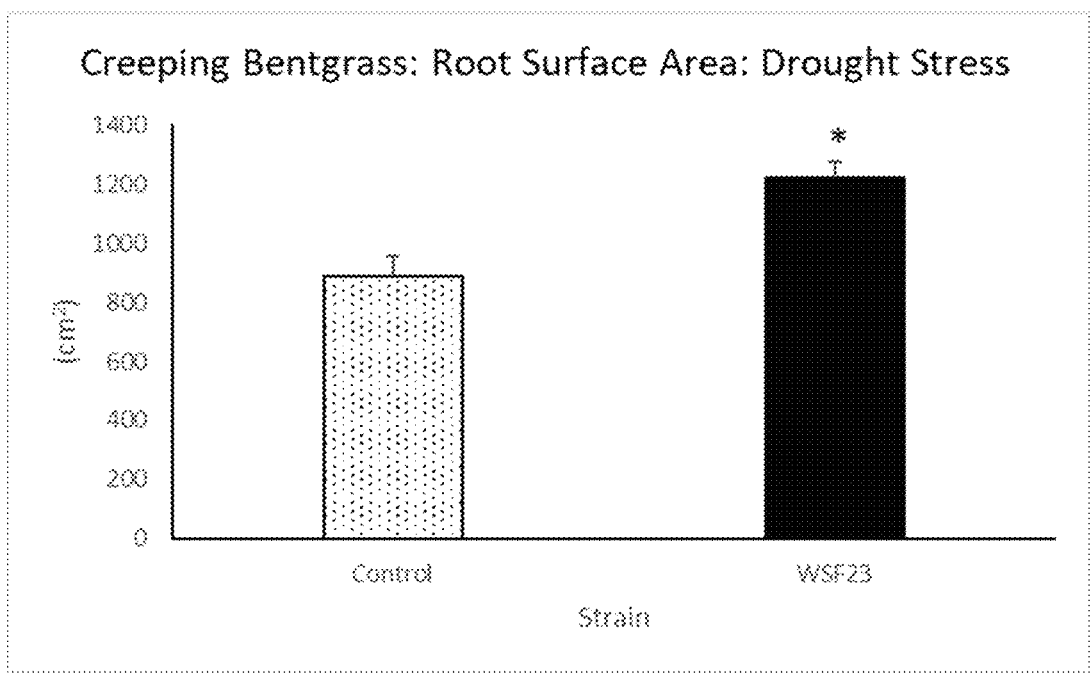
FIGS. 5A-5C. *P. aspalathi* WSF23 improves drought tolerance in creeping bentgrass plants.
Figure 5B:
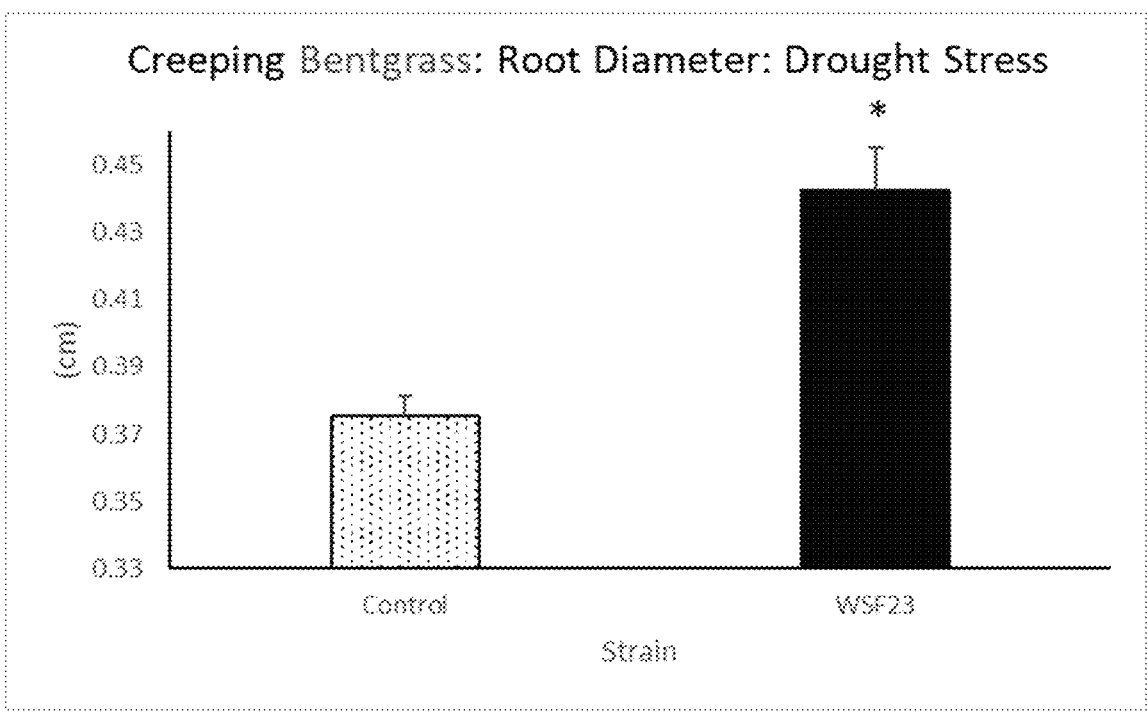
Figure 5C:
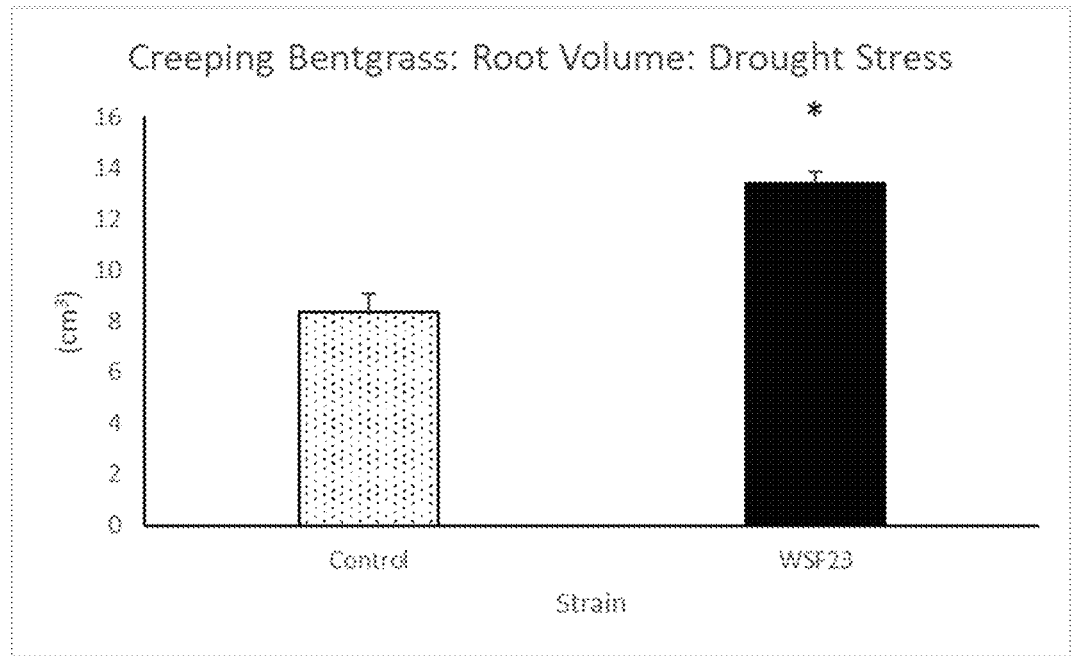

In drought conditions, inoculated plants had increased root surface area, diameter(s) and volume(s) compared to non-inoculated plants. (FIGS. 5A-5C). Under both drought stress and optimum conditions, inoculated plants demonstrated enhanced growth in the 35 days of drought stress or optimal conditions, (FIG. 6A) retaining higher turf quality (FIG. 6B), canopy density, (FIG. 6C), higher dark green color index (FIG. 6D), higher tiller production (FIG. 6E), and a higher rate of tiller production (FIG. 6F). After 35 days under either drought stress or optimum conditions, inoculated plants had lower levels of ACC (FIG. 6G), higher levels of total soluble sugars (FIG. 6H) and greater root viability (FIG. 6I). This data shows that inoculated plants have increased growth in both optimal and drought conditions over the control plant.

After the 35-day period, inoculated and control plants were subjected to a 15-day period of re-watering at optimal conditions. Turf quality, canopy density, DGCI (dark green color index), and tiller production were quantified during the re-watering period. Root biomass, length, surface area, and volume were quantified at the conclusion of the re-watering period.

During the re-watering period, inoculated plants demonstrated enhanced growth (FIG. 7A), retaining higher turf quality (FIG. 7B), canopy density, (FIG. 7C), higher dark green color index (FIG. 7D), higher tiller production (FIG. 7E), and a higher rate of tiller production (FIG. 7F). After the re-watering period, inoculated plants had greater root biomass (FIG. 7G), length (FIG. 7H), surface area (FIG. 7I), volume (FIG. 7J), and diameter (FIG. 7K). This data demonstrates inoculated plant's improved recuperative ability post-drought compared to control plants.

Improved Heat Tolerance

Creeping bentgrass inoculated with WSF23 exhibited physiological and root growth properties characteristic of improved heat tolerance. Inoculated plants had improved turf quality (FIG. 8A), higher membrane stability (FIG. 8B), increased photochemical efficiency (FIG. 8C), and increased root diameter(s) (FIG. 8D) compared to non-inoculated plants.

Example III

Use of *P. aspalathi* Strains as Biofertilizer

The present invention contemplates a synthetic combination of a plant element that is associated with a single bacteria strain or a plurality of bacterial strains to confer an improved trait of agronomic importance to the host plant, or an improved agronomic trait potential to a plant element associated with the bacterial strains, that upon and after germination will confer said benefit to the resultant host plant.

In some embodiments, the plant element is a leaf, and the synthetic combination is formulated for application as a foliar treatment.

In some embodiments, the plant element is a seed, and the synthetic combination is formulated for application as a seed coating.

In some embodiments, the plant element is a root, and the synthetic combination is formulated for application as a root treatment.

In certain embodiments, the plant element becomes associated with a plurality of bacterial strains through delayed exposure. For example, the soil in which a plant element is to be introduced is first treated with a composition comprising a plurality of bacterial strains. In another example, the area around the plant or plant element is exposed to a formulation comprising a plurality of bacterial strains, and the plant element becomes subsequently associated with the bacterial strain(s) due to movement of soil, air, water, insects, mammals, human intervention, or other methods.

The plant element can be obtained from any agricultural plant. In some embodiments, the plant element of the first plant is from a monocotyledonous plant. For example, the plant element of the first plant is from a cereal plant. The plant element of the first plant can be selected from the group consisting of a maize seed, a wheat seed, a barley seed, a rice seed, a sugarcane seed, a maize root, a wheat root, a barley root, a sugarcane root, a rice root, a maize leaf, a wheat leaf, a barley leaf, a sugarcane leaf, or a rice leaf. In an alternative embodiment, the plant element of the first plant is from a dicotyledonous plant. The plant element of the first plant can be selected from the group consisting of a cotton seed, a tomato seed, a canola seed, a pepper seed, a soybean seed, a cotton root, a tomato root, a canola root, a pepper root, a soybean root, a cotton leaf, a tomato leaf, a canola leaf, a pepper leaf, or a soybean leaf. In still another embodiment, the plant element of the first plant can be from a genetically modified plant. In other embodiments, the plant element of the first plant can be a hybrid plant element.

A single bacteria strain or a plurality of bacterial strains is intended to be useful in the improvement of agricultural plants, and as such, may be formulated with other compositions as part of an agriculturally compatible carrier. It is contemplated that such carriers can include, but not be limited to: seed treatment, root treatment, foliar treatment, soil treatment. The carrier composition with a plurality of bacterial strains, may be prepared for agricultural application as a liquid, a solid, or a gas formulation. Application to the plant may be achieved, for example, as a powder for surface deposition onto plant leaves, as a spray to the whole plant or selected plant element, as part of a drip to the soil or the roots, or as a coating onto the seed prior to planting. Such examples are meant to be illustrative and not limiting to the scope of the invention.

In some embodiments, the present invention contemplates plant elements comprising a single bacteria strain or a plurality of bacterial strains, and further comprising a formulation. The formulation useful for these embodiments generally comprises at least one member selected from the group consisting of an agriculturally compatible carrier, a tackifier, a microbial stabilizer, a fungicide, an antibacterial agent, an herbicide, a nematicide, an insecticide, a plant growth regulator, a rodenticide, and a nutrient.

In some cases, a single bacteria strain or a plurality of bacterial strains is mixed with an agriculturally compatible carrier. The carrier can be a solid carrier or liquid carrier. The carrier may be any one or more of a number of carriers described herein that confer a variety of properties, such as increased stability, wettability, or dispersability. Wetting agents such as natural or synthetic surfactants, which can be nonionic or ionic surfactants, or a combination thereof can be included in a composition of the invention. Water-in-oil emulsions can also be used to formulate a composition that includes one or more bacterial strains. Suitable formulations that may be prepared include wettable powders, granules, gels, agar strips or pellets, thickeners, and the like, micro-encapsulated particles, and the like, liquids such as aqueous flowables, aqueous suspensions, water-in-oil emulsions, etc. The formulation may include grain or legume products, for example, ground grain or beans, broth or flour derived from grain or beans, starch, sugar, or oil.

The agricultural carrier may be soil or plant growth medium. Other agricultural carriers that may be used include fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the cultured organisms, such as barley, rice, or other biological materials such as seed, leaf, root, plant elements, sugar cane bagasse, hulls or stalks from grain processing, ground plant material or wood from building site refuse, sawdust or small fibers from recycling of paper, fabric, or wood. Other suitable formulations will be known to those skilled in the art.

The formulation can also contain a surfactant, wetting agent, emulsifier, stabilizer, or anti-foaming agent. Non-limiting examples of surfactants include nitrogen-surfactant blends such as Prefer 28 (Cenex), Surf-N (US), Inhance (Brandt), P-28 (Wilfarm) and Patrol (Helena); esterified seed oils include Sun-It II (AmCy), MSO (UAP), Scoil (Agsco), Hasten (Wilfarm) and Mes-100 (Drexel); and organo-silicone surfactants include Silwet L77 (UAP), Silikin (Terra), Dyne-Amic (Helena), Kinetic (Helena), Sylgard 309 (Wilbur-Ellis) and Century (Precision), polysorbate 20, polysorbate 80, Tween 20, Tween 80, Scattics, Alktest TW20, Canarcel, Peogabsorb 80, Triton X-100, Conco NI, Dowfax 9N, Igebapl CO, Makon, Neutronyx 600, Nonipol NO, Plytergent B, Renex 600, Solar NO, Sterox, Serfonic N, T-DET-N, Tergitol NP, Triton N, IGEPAL CA-630, Nonident P-40, and Pluronic. In some embodiments, the surfactant is present at a concentration of between 0.01% v/v to 10% v/v. In other embodiments, the surfactant is present at a concentration of between 0.1% v/v to 1% v/v. An example of an anti-foaming agent is Antifoam-C.

In certain cases, the formulation includes a microbial stabilizer. Such an agent can include a desiccant. As used herein, a "desiccant" can include any compound or mixture of compounds that can be classified as a desiccant regardless of whether the compound or compounds are used in such concentrations that they in fact have a desiccating effect on the liquid inoculant. Such desiccants are ideally compatible with the bacterial strains used and should promote the ability of the microbial population to survive application on the plant elements and to survive desiccation. Examples of suitable desiccants include one or more of trehalose, sucrose, glycerol, and Methylene glycol. Other suitable desiccants include, but are not limited to, non-reducing sugars and sugar alcohols (e.g., mannitol or sorbitol). The amount of desiccant introduced into the formulation can range from about 5% to about 50% by weight/volume, for example, between about 10% and about 40%, between about 15% and about 35%, or between about 20% and about 30%.

In the liquid form, for example, solutions or suspensions, a plurality of bacterial strains can be mixed or suspended in aqueous solutions. Suitable liquid diluents or carriers include aqueous solutions, petroleum distillates, or other liquid carriers.

Solid compositions can be prepared by dispersing one or more of the bacteria of the invention in and on an appropriately divided solid carrier, such as peat, wheat, bran, vermiculite, clay, talc, bentonite, diatomaceous earth, fuller's earth, pasteurized soil, and the like. When such formulations are used as wettable powders, biologically compatible dispersing agents such as non-ionic, anionic, amphoteric, or cationic dispersing and emulsifying agents can be used.

The solid carriers used upon formulation include, for example, mineral carriers such as kaolin clay, pyrophyllite, bentonite, montmorillonite, diatomaceous earth, acid white soil, vermiculite, and pearlite, and inorganic salts such as ammonium sulfate, ammonium phosphate, ammonium nitrate, urea, ammonium chloride, and calcium carbonate. Also, organic fine powders such as wheat flour, wheat bran, and rice bran may be used. The liquid carriers include vegetable oils such as soybean oil and cottonseed oil, glycerol, ethylene glycol, polyethylene glycol, propylene glycol, polypropylene glycol, etc.

In some embodiments, the formulation is ideally suited for coating of a plurality of bacteria onto plant elements. The plurality of bacteria is capable of conferring many agronomic benefits to the host plants. The ability to confer such benefits by coating the plurality of bacteria on the surface of plant elements has many potential advantages, particularly when used in a commercial (agricultural) scale.

In certain embodiments, a composition described herein may be in the form of a liquid, a slurry, a solid, or a powder (wettable powder or dry powder). In another embodiment, a composition may be in the form of a seed coating. Compositions in liquid, slurry, or powder (e.g., wettable powder) form may be suitable for coating plant elements. When used to coat plant elements, the composition may be applied to the plant elements and allowed to dry. In embodiments wherein the composition is a powder (e.g., a wettable powder), a liquid, such as water, may need to be added to the powder before application to a seed.

In still another embodiment, the methods can include introducing into the soil an inoculum of one or more of the bacteria populations described herein. Such methods can include introducing into the soil one or more of the compositions described herein. The inoculum(s) or compositions may be introduced into the soil according to methods known to those skilled in the art. Non-limiting examples include in-furrow introduction, spraying, coating seeds, foliar introduction, etc. In a particular embodiment, the introducing step comprises in-furrow introduction of the inoculum or compositions described herein.

In one embodiment, plant elements may be treated with composition(s) described herein in several ways but preferably via spraying or dripping. Spray and drip treatment may be conducted by formulating compositions described herein and spraying or dripping the composition(s) onto a seed(s) via a continuous treating system (which is calibrated to apply treatment at a predefined rate in proportion to the continuous flow of seed), such as a drum-type of treater.

Batch systems, in which a predetermined batch size of seed and composition(s) as described herein are delivered into a mixer, may also be employed. Each of the aforementioned applications can be applied in the laboratory, in a green house or in field conditions.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A microbial inoculant biofertilizer composition comprising at least one microbial strain selected from *P. aspalathi* WSF14 comprising a nucleic acid sequence having at least 98% identity to SEQ ID NO: 1, and *P. aspalathi* WSF23 comprising a nucleic acid sequence having at least 98% identity to SEQ ID NO: 2, and at least one non-naturally occurring agent, wherein the agent is least one of a cell protectant, an inert, a carrier, an emulsifier, a surfactant and a polymeric matrix, wherein the at least one microbial strain is present at an effective amount to promote plant health, plant nutrition, and/or soil health in the presence of said agent.

2. The biofertilizer composition according to claim 1, wherein at least one or more microbial species is lyophilized and optionally, encapsulated.

3. The biofertilizer composition of claim 1, wherein the composition further comprises one or more of mineral nutrients, amino acids, sugars, hormones, and organic acids.

4. The biofertilizer composition of claim 1, wherein the composition is in a liquid formulation.

5. The biofertilizer composition of claim 1, wherein the composition comprises a carrier.

6. The biofertilizer composition of claim 1, wherein the composition comprises a cell protectant.

7. The composition of claim 1, comprising *P. aspalathi* WSF14 and *P. aspalathi* WSF23 having a nucleic acid sequence having at least 99% identity to SEQ ID NO: 1 and SEQ ID NO:2 respectively.

8. A method for increasing plant growth and/or productivity, the method comprising applying to a plant, plant part, plant seed, or to a soil in which the plant or plant seeds are grown an effective amount of a microbial inoculant biofertilizer composition according to claim 1.

9. The method of claim 8, wherein said bacteria enhance resistance of said plant to abiotic stress, relative to untreated control plants.

10. The method of claim 9, wherein said stress is selected from drought stress, heat stress, cold stress and salinity stress.

11. The method of claim 8, wherein the composition further comprises one or more of mineral nutrient elements, amino acids, sugars, hormones, and organic acids.

12. The method of claim 8, wherein applying comprises contacting soil in the immediate vicinity of a plant, seedling, or seed with an effective amount of the biofertilizer composition.

13. The method of claim 12, wherein each of said *P. aspalathi* WSF14 and *P. aspalathi* WSF23 are present.

14. The method of claim 8, wherein the bacteria are present in a seed ball.

15. The method of claim 8, wherein said bacteria comprises a nucleic acid sequence having at least 99% identity to SEQ ID NO: 1.

16. The method of claim 8, wherein said bacteria comprises a nucleic acid sequence having at least 99% identity to SEQ ID NO: 2.

17. A method of enhancing a yield trait in a subject plant as compared to the yield trait of a reference or control plant, the method comprising contacting the subject plant, plant part, plant seed, or surrounding soil with the biofertilizer composition of claim 1 at the effective amount wherein said contacting is effective in enhancing the yield trait in the subject plant relative to the yield trait observed in the untreated reference or control plant.

18. A method of treating soil to improve plant growth, comprising applying the biofertilizer composition of claim 1 to said soil in an effective amount to improve growth of plants in said treated soil relative to plant growth observed in untreated soil.

*    *    *    *    *

SEQUENCE LISTING

```
<160> NUMBER OF SEQ ID NOS: 2

<210> SEQ ID NO 1
<211> LENGTH: 781
<212> TYPE: DNA
<213> ORGANISM: Paraburkholderia aspalathi

<400> SEQUENCE: 1
aattccacgt gtagcagtga aatgcgtaga gatgtggagg aataccgatg gcgaaggcag       60
cccccctggg ccaatactga cgctcatgca cgaaagcgtg gggagcaaac aggattagat      120
accctggtag tccacgccct aaacgatgtc aactagttgt tggggattca tttccttagt      180
aacgtagcta acgcgtgaag ttgaccgcct ggggagtacg gtcgcaagat taaaactcaa      240
aggaattgac ggggacccgc acaagcggtg gatgatgtgg attaattcga tgcaacgcga      300
aaaaccttac ctaccttga catgtatgga accctgctga gaggtggggg tgcccgaaag       360
ggagccataa cacaggtgct gcatggctgt cgtcagctcg tgtcgtgaga tgttgggtta      420
agtcccgcaa cgagcgcaac ccttgtccct agttgctacg caagagcact ctagggagac      480
tgccggtgac aaaccggagg aaggtgggga tgacgtcaag tcctcatggc ccttatgggt      540
agggcttcac acgtcataca atggtcggaa cagagggtcg ccaacccgcg aggggagcc       600 aatcccagaa aaccgatcgt agtccggatc gcactctgca actcgagtgc gtgaagctgg      660
aatcgctagt aatcgcggat cagcatgccg cggtgaatac gttcccgggt cttgtacaca      720
ccgcccgtca caccatggga gtgggttta ccagaagtgg ctagtctaac cgcaaggagg       780
a                                                                       781

<210> SEQ ID NO 2
<211> LENGTH: 772
<212> TYPE: DNA
<213> ORGANISM: Paraburkholderia aspalathi

<400> SEQUENCE: 2
gtagcagtga aatgcgtaga gatgtggagg aataccgat ggcgaaggca gcccccctggg       60 ccaatactga cgctcatgca cgaaagcgtg gggagcaaac aggattagat accctggtag      120
tccacgccct aaacgatgtc aactagttgt tggggattca tttccttagt aacgtagcta      180
acgcgtgaag ttgaccgcct ggggagtacg gtcgcaagat taaaactcaa aggaattgac      240
ggggacccgc acaagcggtg gatgatgtgg attaattcga tgcaacgcga aaaaccttac      300 ctaccttga catgtatgga accctgctga gaggtggggg tgcccgaaag ggagccataa       360
cacaggtgct gcatggctgt cgtcagctcg tgtcgtgaga tgttgggtta agtcccgcaa      420
cgagcgcaac ccttgtccct agttgctacg caagagcact ctagggagac tgccggtgac      480
aaaccggagg aaggtgggga tgacgtcaag tcctcatggc ccttatgggt agggcttcac      540
```

-continued

```
acgtcataca atggtcggaa cagagggtcg ccaacccgcg aggggggagcc aatcccagaa    600 aaccgatcgt agtccggatc gcactctgca actcgagtgc gtgaagctgg aatcgctagt    660
aatcgcggat cagcatgccg cggtgaatac gttcccgggt cttgtacaca ccgcccgtca    720
caccatggga gtgggtttta ccagaagtgg ctagtctaac cgcaaggagg ac           772
```